US008921440B2

(12) United States Patent
Weinmann et al.

(10) Patent No.: US 8,921,440 B2
(45) Date of Patent: *Dec. 30, 2014

(54) RADIATION CURABLE COMPOSITION, PROCESS OF PRODUCTION AND USE THEREOF

(75) Inventors: Wolfgang Weinmann, Wilheim (DE); Joachim W. Zech, Kaufering (DE); Wolf Steiger, Geretsried (DE); Arne Thaler, Emmerting (DE)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/640,342

(22) PCT Filed: Apr. 19, 2011

(86) PCT No.: PCT/US2011/032962
§ 371 (c)(1), (2), (4) Date: Oct. 10, 2012

(87) PCT Pub. No.: WO2011/133495
PCT Pub. Date: Oct. 27, 2011

(65) Prior Publication Data
US 2013/0030076 A1 Jan. 31, 2013

(30) Foreign Application Priority Data
Apr. 22, 2010 (EP) .................... 10160707

(51) Int. Cl.
| | |
|---|---|
| *C08G 59/68* | (2006.01) |
| *B29C 71/04* | (2006.01) |
| *C08F 2/50* | (2006.01) |
| *C08F 2/46* | (2006.01) |
| *A61L 2/08* | (2006.01) |
| *A61L 24/00* | (2006.01) |
| *C08G 61/04* | (2006.01) |
| *C08K 5/00* | (2006.01) |
| *C08L 101/02* | (2006.01) |

(52) U.S. Cl.
CPC ........... *C08K 5/0025* (2013.01); *C08L 101/025* (2013.01)
USPC ........ 522/31; 522/6; 522/71; 522/1; 522/189; 522/184; 520/1

(58) Field of Classification Search
CPC ............ C08F 2/50; C08F 2/48; C08F 255/02; G03F 7/027; G03F 7/025; A61K 6/0047
USPC .................. 522/31, 6, 71, 1, 189, 184; 520/1
See application file for complete search history.

(56) References Cited

U.S. PATENT DOCUMENTS

| | | | |
|---|---|---|---|
| 3,453,242 A | 7/1969 | Schmitt | |
| 3,729,313 A | 4/1973 | Smith | |
| 3,741,769 A | 6/1973 | Smith | |
| 3,808,006 A | 4/1974 | Smith | |
| 3,926,636 A | 12/1975 | Barzynski | |
| 4,167,618 A | 9/1979 | Schmitt | |
| 4,250,053 A | 2/1981 | Smith | |
| 4,394,403 A | 7/1983 | Smith | |
| 4,642,126 A | 2/1987 | Zador | |
| 4,652,274 A | 3/1987 | Boettcher | |
| 4,657,959 A | 4/1987 | Bryan | |
| 4,768,951 A | 9/1988 | Abiru | |
| 4,790,752 A | 12/1988 | Cheslak | |
| 5,249,862 A | 10/1993 | Herold | |
| 5,286,105 A | 2/1994 | Herold | |
| 5,419,460 A | 5/1995 | Herold | |
| 5,464,131 A | 11/1995 | Keller | |
| 5,487,662 A | 1/1996 | Kipke | |
| 5,569,691 A | 10/1996 | Guggenberger | |
| 5,624,260 A | 4/1997 | Wilcox | |
| 5,702,250 A | 12/1997 | Kipke | |
| 5,718,577 A | 2/1998 | Oxman | |
| 5,750,589 A | 5/1998 | Zech | |
| 5,865,803 A | 2/1999 | Major | |
| 5,893,714 A | 4/1999 | Arnold | |
| 5,918,772 A | 7/1999 | Keller | |
| 6,043,295 A | 3/2000 | Oxman | |
| 6,045,974 A * | 4/2000 | Cunningham et al. | 430/281.1 |

(Continued)

FOREIGN PATENT DOCUMENTS

| | | |
|---|---|---|
| EP | 0232733 | 2/1986 |
| EP | 0231420 | 8/1987 |

(Continued)

OTHER PUBLICATIONS

Ishizone et al., "Synthesis of New Crosslinkable Polymers by Chemoselective Polymerizations of 2-(1-Aziridinyl)ethyl Methacrylate," *Journal of Polymer Science: Part A: Polymer Chemistry*, 2003; 41:1335-1340.

Saldivar-Guerra et al., *Handbook of Polymer Synthesis, Characterization, and Processing*, Hoboken, NJ 2013; Schemes 8.22 & 8.23; 1 page.

Tebaldi de Sordi et al., "Synthesis and radical polymerization of bifunctionalized aziridinic metacrylates," *Reactive & Functional Polymers*, 2011; 71:648-654.

Extended Search Report for EP 10 16 0707 dated Nov. 24, 2010.

Falbe, R. 1991. *Römpp Chemie Lexikon*. 9:3114. Georg Thieme Verlag, Stuttgart: New York. XP002610975. ISBN: 3-13-734909-5. "Oninium-Verbindungen".

(Continued)

*Primary Examiner* — Ling Choi
*Assistant Examiner* — Jessica E Whiteley
(74) *Attorney, Agent, or Firm* — 3M Innovative Properties Company; Qiang Han

(57) ABSTRACT

The invention relates to a radiation curable composition for taking a dental impression comprising (A) a cationically hardenable compound comprising at least one aziridine moiety, and (B) a radiation sensitive starter, the radiation sensitive starter comprising an onium salt, a ferrocenium salt, a combination or mixture thereof.

15 Claims, No Drawings

(56) References Cited

U.S. PATENT DOCUMENTS

| | | | |
|---|---|---|---|
| 6,084,004 A | 7/2000 | Weinmann | |
| 6,127,449 A | 10/2000 | Bissinger | |
| 6,135,631 A | 10/2000 | Keller | |
| 6,244,740 B1 | 6/2001 | Wagner | |
| 6,395,801 B1 | 5/2002 | Bissinger | |
| 6,420,607 B1 * | 7/2002 | Hamrock et al. | 568/32 |
| 6,599,960 B1 | 7/2003 | Eckhardt | |
| 6,930,134 B2 * | 8/2005 | Suzuki et al. | 522/25 |
| 6,932,882 B2 * | 8/2005 | Haruta et al. | 156/306.3 |
| 2001/0004082 A1 | 6/2001 | Keller | |
| 2003/0153726 A1 | 8/2003 | Eckhardt | |
| 2004/0085854 A1 | 5/2004 | Pauser | |
| 2004/0146713 A1 | 7/2004 | Schaub | |
| 2004/0149164 A1 | 8/2004 | Eckhardt | |
| 2004/0186195 A1 * | 9/2004 | Suzuki et al. | 522/31 |
| 2005/0200585 A1 | 9/2005 | Igarashi | |
| 2006/0069180 A1 | 3/2006 | Bublewitz | |
| 2006/0106127 A1 | 5/2006 | Klettke | |
| 2007/0090079 A1 | 4/2007 | Kelller | |
| 2007/0172789 A1 | 7/2007 | Muller | |
| 2008/0200585 A1 * | 8/2008 | Klettke et al. | 523/109 |
| 2010/0230351 A1 * | 9/2010 | Hoving et al. | 210/650 |
| 2012/0064482 A1 | 3/2012 | Boehm | |
| 2012/0077900 A1 | 3/2012 | Maurer | |

FOREIGN PATENT DOCUMENTS

| | | | |
|---|---|---|---|
| EP | 0678282 | | 10/1995 |
| EP | 0758662 | | 2/1997 |
| EP | 0863088 | | 9/1998 |
| EP | 0886498 | | 12/1998 |
| EP | 1340472 | | 9/2003 |
| EP | 1431315 | | 6/2004 |
| EP | 1748057 | | 1/2007 |
| WO | WO 97/33528 | | 9/1997 |
| WO | WO 2005/016783 | | 2/2005 |
| WO | WO 2007/016295 | | 2/2007 |
| WO | WO 2007/047381 | | 4/2007 |
| WO | WO 2007/104037 | | 9/2007 |
| WO | 2008/014224 | * | 1/2008 |
| WO | WO 2008/014224 | * | 1/2008 |
| WO | WO 2009/061884 | | 5/2009 |
| WO | WO 2009/151983 | | 12/2009 |

OTHER PUBLICATIONS

International Search Report for PCT/US2011/032962 mailed Jun. 24, 2011.
Ullmanns Enzyklopädie der industriellen Chemie. 4th Edition, vol. 11, p. 469, 1984.
Ullmanns Enzyklopädie der technischen Chemie. 4$^{th}$ Edition, vol. 11, Band 24, p. 3, 1984.
*Inter alia*, "Houben-Weyl, Methoden der Organischen Chemie," vol. E5/Part 1, p. 659-663 ff, 1985.

\* cited by examiner

RADIATION CURABLE COMPOSITION, PROCESS OF PRODUCTION AND USE THEREOF

CROSS REFERENCE TO RELATED APPLICAIONS

This application is a national stage filing under 35 U.S.C. 371 of PCT/US2011/032962, filed Apr. 19, 2011, which claims priority to European Application No. 10160707.5, filed Apr. 22, 2010, the disclosures of which are incorporated by reference in their entirety herein.

FIELD OF THE INVENTION

The invention relates to a radiation curable composition comprising a cationically hardenable compound with one or more aziridine groups and a radiation sensitive starter composition. The composition is particularly useful in various fields or for producing a wide variety of materials including bondings, coatings, printing inks, dental materials, photo resists.

BACKGROUND ART

Polymeric compositions can be obtained in various ways. Curing mechanisms known in the art include radical polymerization, cationic polymerization and anionic polymerization. The curing reaction can be started by different means including heat, radiation or simply by mixing two reactive components containing redox-active substances.

Besides other areas curable compositions can also be used in the dental field, e.g. as dental impression materials.

Dental impression materials are used to record the oral situation of a patient. The resulting hardened impression material captures the negative of the oral situation.

Most dental impression materials are typically delivered in a two or more paste form, containing a base paste and a catalyst paste, which are mixed prior to their application. The mixed pastes are typically applied with the help of a dental tray and/or a syringe-type device. Usually the hardened material can be removed after about one to about six minutes after application. The hardened impression material is used either for making a provisional restoration using a temporary crown and bridge material or for producing a positive model of the oral situation by casting the mould with e.g. gypsum. The obtained positive model is used for making the final restoration in the dental laboratory.

Different types of chemistry can be employed to formulate impression materials. Often used are polyether impression materials which cure by a cationic ring-opening polymerization of aziridines (e.g. Impregum™, 3M ESPE), polysiloxanes which cure via a hydrosilation reaction (e.g. Imprint™, 3M ESPE), polysiloxanes which cure via a condensation mechanism (e.g. Xantropren™, Heraeus Kulzer), mixtures of polyethers and siloxanes which cure via a hydrosilation mechanism (e.g. Senn™, GC) and polyethers which cure via a condensation mechanism (e.g. P2™, Heraeus Kulzer).

Aziridino moiety containing components are typically cured by using strong acids.

Strong acids which can be used include substances like sulfonium salts, especially alkyl sulfonium salts or sulfonium salts derived from glutaconic acid. Those and others are described e.g. in US 2008/0200585 A1, U.S. Pat. No. 4,167,618 and US 2003/0153726 A1.

Aziridine containing prepolymers are used i.a. in the dental field, especially for producing dental impression materials.

The curing reaction of the aziridino moieties containing impression material is typically started by mixing a base paste containing the aziridino moieties bearing prepolymer and a catalyst paste containing a strong acid, especially a Lewis acid.

In this respect, US 2004/0149164 relates to a mixture of elongated N-alkylaziridine prepolymers which can be used as a dental material. The mixture can contain various modifiers like finely divided fillers, pigments, thixotropic agents and surface-active substances.

U.S. Pat. No. 6,599,960 relates to storage-stable cationically polymerized preparations with improved hardening characteristics. The preparations can contain 0.0005 to 50 wt.-% of soluble and/or fine-particle organic and/or inorganic alkaline earth and/or alkali metal compounds. The preparation can be used for making dental impressions.

U.S. Pat. No. 3,926,636 relates to a light-curable composition consisting of a substance containing at least two aromatic or heteroaromatic o-nitrocarbinol ester groups of a certain structure and a compound having at least two aziridine groups or isocyanate groups. The light-curable composition is particularly suitable for the production of coatings and printing plates.

EP 0758 662 A2 (Rockwell) describes a curable epoxy composition containing aziridine and a catalyst to promote curing at ambient temperature. Four classes of catalysts are described. Curing is effected by mixing the curable epoxy resin system with the catalyst. The epoxy resin system is said to have utility as adhesive and coating.

U.S. Pat. No. 4,167,618 (Schmitt) relates to a polymerization process for aziridine compounds. The polymerization process includes mixing an aziridine compound with an alkyl sulfonium salt.

EP 1 431 315 A2 (Tokuyama) relates to a polymerization initiator capable of polymerizing both a cationically polymerizable monomer and a radically polymerizable monomer. The photopolymerizable composition is said to be useful in the dental field, especially as a dental adhesive or as a dental filler restorative.

Especially from a practitioner's standpoint of view it would be desirable to have a material at hand, which can be cured on demand, especially a material which can be applied on a certain surface, adjusted according to the practitioner's needs, and cured when desired.

SUMMARY OF INVENTION

In one embodiment, the invention features a radiation curable composition comprising
  a cationically hardenable compound comprising at least one or at least two aziridine moieties, and
  a radiation sensitive starter composition, a radiation sensitive starter, the radiation sensitive starter comprising an onium salt (including sulfonium and iodonium salts), a ferrocenium salt, a combination or mixture thereof.

In another embodiment, the invention features a process of producing such a composition comprising a mixing step.

The invention is also directed to a kit of parts comprising part I and part II, part I comprising the cationically hardenable compound comprising at least one or at least two aziridine moieties and part II comprising the radiation sensitive starter.

According to a further embodiment, the invention is directed to a kit of parts comprising a composition A having the consistency A and a composition B having the consistency B, consistency A and consistency B being different from each other and the composition B being as described in the text of the invention.

A further embodiment of the invention is directed to the use of the composition as described in the text of the invention as or for producing adhesive(s), coating(s), imaging layer(s), photo resist(s), dental material(s), Moreover, the invention features a method of taking an impression of dental tissue, comprising the steps of
a) providing a composition A having the consistency A and a composition B having the consistency B, consistency A and consistency B being different from each other and composition B being as described in the text of the invention,
b) bringing composition B into contact with a surface,
c) applying radiation on composition B,
d) bringing composition A into contact with composition B,
e) removing composition A and composition B from the surface.

It has been found that the composition described in the text of the invention fulfils the practitioners' needs especially with regard to properties like curing time and/or depth of cure.

Certain embodiments may also fulfil the practitioners' needs with respect to Shore hardness A, tear strength and/or short and controllable working time The inventive composition can be cured on demand. That is the practitioner has the time he needs for applying the curable composition on a substrate or surface. If he is satisfied, he can start the curing process by applying radiation.

Surprisingly, it was found that the basic amine in the aziridine group does not negatively interfere with the radiation sensitive initiator used.

From a chemical standpoint of view one would have expected that the resulting open chained amino groups stop or at least retard the polymerization reaction significantly. As known to the person skilled in the art, combining acids and bases typically leads to a neutralisation.

In contrast to this, it has been observed that this is not the case.

The inventive composition can be cured by ambient conditions, including room temperature.

Certain compositions of the invention also do not require a mixing step.

The surface of certain compositions is typically tack free after curing.

Certain embodiments of the inventive composition may also have a sufficient shelf life, that is, they can be stored for a sufficient period of time without negatively affecting the desired properties.

Thus, a curable composition can be provided where the curable components are present together with the initiator(s) in a mixture. Absent radiation, the mixture remains storage stable. However, upon radiation the mixture starts to cure.

Depending on the chosen backbone of the prepolymer bearing the aziridine group(s), the inventive composition can be highly hydrophilic.

Certain embodiments show a useful combination of high cure speed, high cure depth, and temperature insensitivity.

Within the description of the invention, the following terms are defined as follows:

The term "compound" is a chemical substance which has a particular molecular identity or is made of a mixture of such substances, e.g., polymeric substances.

By "paste" is meant a soft, viscous mass of solids dispersed in at least one liquid or a soft, viscous mass of a polymer.

A "hardenable compound" is any compound which can be cured or solidified e.g. by chemical crosslinking. Chemical crosslinking can be initiated by using a redox or ionic initiator, radiation or heating thereby typically leading to a significant change in rheological properties like viscosity.

A "starter or initiator" is a substance or a group of substances being able to start or initiate the hardening process of a hardenable compound.

"Radiation sensitive" means that the composition or a part of the composition is sensitive towards radiation and generates or helps to generate reactive species when exposed to the radiation. Those reactive species typically include radicals (charged or not charged), ions and mixtures thereof.

"Radiation curable" means that the composition can be cured or hardened using radiation alone or in combination with other initiators or starters, including redox initiators. The radiation typically comprises wavelength in the range from about 250 to about 1000 nm or from about 350 nm to about 700 nm.

The terms "vulcanizing", "hardening", "polymerizing", "crosslinking", "curing" and "setting" are used interchangeable and refer to compositions that have as a common attribute the development of a crosslinked polymer from relatively low molecular weight linear or branched polymers or pre-polymers by means of a chemical reaction that simultaneously forms these crosslinks and effectively extends chain length at room temperature.

The term "crosslinked polymer" refers to polymers that are the result of the reaction of the functional group or groups of the polymer chains or prepolymers that were lengthened or connected, e.g., to form a crosslinked network. In contrast to a thermoplastic polymer (i.e., a polymer that softens and flows upon heating) a crosslinked polymer, after crosslinking, is characteristically incapable of further flow.

"Elastomeric" means rubber-elastic or rubber-like. Elastomeric materials can be characterized e.g. by a certain tensile strength and/or elongation at break. Other means for characterizing elastomeric materials include the measurement e.g. of the Young's modulus. Elastomeric materials according to the invention typically have an E-modulus in the range from about 0.8 to about 10 MPa or from about 1 to about 8 MPa or from about 1.5 to about 6 MPa (determined e.g. according to DIN 53504, thickness of sample: 2 mm).

The term "cationically polymerizable compound" is defined as a compound which can be polymerised using an initiator containing or being able to generate cations, especially reactive cations.

A "prepolymer" is defined as a compound or a mixture of compounds obtainable by polymerization (such as e.g. polycondensation reaction) of monomers resulting in an intermediate product or mixture of products with increased molecular weight compared to the monomers used. The resulting intermediate product itself bears functional groups (either left over from the initial polymerization or introduced afterwards). The prepolymer containing functional groups can be used for further polymerization reactions (such as e.g. polycondensation reaction or polyaddition reaction) leading to a polymer or polymer mixture or a crosslinked polymer with increased molecular weight compared to the prepolymer.

"Aziridines" are a group of organic compounds sharing the aziridine functional group which is a three membered heterocycle with one amine group and two methylene groups. The parent compound of the aziridines is called aziridine with molecular formula $C_2H_5N$.

An "alkyl-substituted aziridino group" is an aziridine group, wherein at least one of the hydrogen atoms of the methylene groups is substituted by an alkyl group, preferably by a C1 to C4 alkyl group, e.g. methyl, ethyl, n- and iso-propyl or n-, iso- or tert.-butyl group. In the chemical literature a "methyl substituted aziridine" is sometimes also referred to as "propylene imine".

"Polyether" or "polyether group containing compound" are compounds having a molecular weight of at least about 150 g/mol and containing in the backbone at least about 3, 10 or 20 ether moieties. Polyether containing compositions used as dental impression material can be cured by different mechanisms. Widely used is a crosslinking reaction using aziridine groups.

Examples of polyether groups containing impression materials are given in U.S. Pat. No. 5,569,691, US 2004/0146713 A1 and US 2006/0069180. Commercially available materials are sold e.g. under the brand Impregum™ (3M ESPE).

By "derivative" is meant a chemical compound showing a chemical structure closely related to the corresponding reference compound and containing all featured structural elements of the corresponding reference compound but having small modifications like bearing in addition comparably small additional chemical groups like e.g. $CH_3$, Br, Cl, or F or not bearing comparably small chemical groups like e.g. $CH_3$ in comparison to the corresponding reference compound. The following examples might illustrate this: tetramethyl bis-phenol A bearing four additional methyl groups with respect to the reference compound bis-phenol A, and bisphenol F not bearing two additional methyl groups with respect to the reference compound bis-phenol A are derivatives of bis-phenol A within the meaning of this definition.

A "particle" means a substance being a solid having a shape which can be geometrically determined. The shape can be regular or irregular. Particles can typically be analysed with respect to e.g. grain size and grain size distribution. Fillers typically comprise, essentially consist of or consist of particles.

"Room temperature curable" implies that the curing reaction can proceed at temperatures at or near about 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is retarded) at room temperature for prolonged periods. The compositions of the invention are room temperature vulcanizing.

By "dental composition" is meant a composition which is intended and adapted to be used in the dental field (including restorative and prosthodontic work) including the orthodontic area. In this respect, a dental composition typically does not contain hazardous substances. Commercially available dental impressioning products have to fulfil requirements such as those given in ISO 4823. Typically, those compositions cure or set at ambient conditions.

A "dental impression" may be described as an accurate representation of part or all of a person's dentition. It forms a "negative" of a person's hard dental tissue which can then be used to make a model (physical) of the dentition. This may be used for the fabrication of dentures, crowns or other prostheses. An impression is typically carried out by placing a viscous material into the mouth in a customised or stock tray. The material then sets to become an elastic solid, and when removed from the mouth retains the shape of the teeth and gingiva. Common materials used for dental impressions include alginate, agar, polyethers including aziridine substituted polyether materials as well as silicones, both condensation-cured silicones and addition-cured silicones including polyvinyl siloxanes.

The term "dental tissue" includes the hard tooth substance (enamel and dentin), the gingival region (soft dental tissue) surrounding the hard tooth substance and hard tooth substance bearing orthodontic appliances.

The term "dental impression materials" comprises precision impression materials, situation impression materials, bite registration materials, duplicating materials (applicable for the duplication of master models, e.g. for all-ceramic restorations requiring a refractory investment model and when inlays, onlays, cantilevers and other precision attachments are being fabricated) and modelling materials (applicable for e.g. reconstructing the gingival, producing crowns and bridges). Duplicating and modelling materials are commercially available e.g. from 3M ESPE AG under the trademarks Reprogum™ or Vestogum™.

The term "automixer-suitable impression material" relates to a multi-component impression material which can be dispensed, for example, from a two-component disposable cartridge through a static mixer, e.g., of SulzerMixpac Company (U.S. Pat. No. 5,464,131, US 2001/0004082) or from tubular film bags in dual-chamber reusable cartridges through a dynamic mixer, e.g., in the "Pentamix™", "Pentamix™ 2" and "Pentamix™ 3" devices of 3M ESPE Company (cf. U.S. Pat. No. 5,286,105 and U.S. Pat. No. 5,249,862).

A "temporary crown and bridge material" within the meaning of the invention is a hardenable material used for making dental crowns and bridges. These materials are typically used during the time period a dental technician needs for producing a permanent prosthetic work such as a crown or bridge. These time periods can last from a few days (1 to about 6 days), a few weeks (1 to about 4 weeks) or a few months (1 to about 6 month).

A "surfactant" is an agent imparting wettability to a material, that is making the material more wettable compared to a material not containing a surfactant. The wettabilty can be determined by the water contact angle which can be measured using e.g. a goniometer DSA 10 (Krüss). A low water contact angle indicates a better wettability.

"Molecular weight" in the context of the invention and if not otherwise indicated always means number average molecular weight ($M_n$).

The molecular weight (Mn) of the polymerizable compound before setting can be determined using nuclear magnetic resonance spectroscopy (end-group determination). In this respect proton ($^1H$) NMR techniques are employed to estimate the molecular weight of the precursor of the prepolymer. Integrated signals of the terminal —$CH_2$— groups are compared to the integrated sum of proton signals from backbone hydrocarbon protons taking into account co-monomer ratio, if applicable. To achieve appropriate separation of terminal methylene proton signals from the backbone proton signals, terminal hydroxyl groups are esterified with trifluoroacetic acid.

"Ambient conditions" within the meaning of the invention mean the conditions which the inventive solution is usually subjected to during storage and handling. Ambient conditions may for example. be a pressure of about 900 to about 1100 mbar. a temperature of about −10 to about 60° C. and a relative humidity of about 10 to about 100%. In the laboratory ambient conditions are adjusted to about 23° C. and about 1013 mbar.

A composition or solution is "essentially or substantially free of" a certain component within the meaning of the invention, if the composition or solution does not contain said component as an essential feature. Thus, said component is not wilfully added to the composition or solution either as such or in combination with other components or ingredient of other components. A composition being essentially free of a certain component usually contains the component in an amount of less than about 1 wt.-% or less than about 0.1 wt.-% or less than about 0.01 wt.-% with respect to the whole composition. Ideally the composition does not contain the said component at all. However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4.5, etc.).

Unless otherwise indicated, all numbers expressing quantities of ingredients, measurement of properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION OF INVENTION

Certain embodiments of the radiation curable composition can be characterized by at least one or more of the following features:
- Consistency (according to ISO 4823): 0, 1, 2 or 3,
- Setting time: within about 15 min after applying radiation at ambient conditions (e.g. 23° C.),
- being rubber-like or elastic.

That is, the hardenable composition (that is, in its uncured state) can show a comparable low viscous behaviour (consistency 3), a medium to high viscosity (consistency 1 or 2) or show a putty-like behaviour (consistency 0).

Certain embodiments of the hardened composition can be characterized by at least one or more of the following features:
- Tensile strength (according to DIN 53504): at least about 0.2 MPa, or at least about 1.0 or from about 0.2 to about 10 or from about 1 to about 7 MPa,
- Elongation at break (according to DIN 53504): at least about 30%, or at least about 50%, or at least about 100%,
- Recovery from deformation (according to ISO 4823): at least about 90%, or at least about 95%, or at least about 98%,
- Shore A hardness (according to DIN 53505; 24 h): equal to or above about 10 or 20 or 30 or 40, wherein a range from about 20 to about 30 or from about 40 to about 70 can be preferred.
- Elastic deformation (according to ISO 4823): from about 0.2 to about 20% or from about 0.5 to about 10%.

If desired, the viscosity can be measured at 23° C. using a Physica/Anton Paar (MCR 300 or MCR 301) device with a plate/plate system (diameter 20 mm) and a slit of 0.2 mm. The viscosity values (Pas) and share stress values (Pa) are recorded for each share rate ($\gamma$ starting from 10 l/s to 100 l/s in 10 l/s and/or 5 l/s steps. For each share rate, a delay of 5 s is used before collecting data. The above mentioned method of measurement corresponds essentially to DIN 53018-1.

If desired, the tensile strength and elongation at break of the compositions can be determined according to DIN 53504. The tensile strength is given in MPa and the elongation in % of the original length. Tensile strength and elongation data are evaluated by tearing six I-shaped specimens with a central unit of 20 mm×4 mm×2 mm in a Zwick Z020 Universal testing machine. Base and catalyst pastes can be mixed through a static mixer (e.g. SulzerMixpac Comp.), by an automatic mixing device (e.g. Pentamix™; 3M ESPE) or by hand and filled into a brass mould. After 24 h at about 23° C. the specimen are removed, six measurements are made and the mean value determined (speed 200 mm/min).

The cationically hardenable compound typically comprises a backbone and at least one reactive functional group.

The backbone of the cationically hardenable compound typically comprises moieties selected from polyether, polyester, polyurethane, silicone, polyalkylene, polystyrol, polysulfide and combinations thereof.

In the dental field a polyether moieties containing backbone can be preferred. Those groups typically also improve the hydrophilic properties of the composition.

According to one embodiment, the cationically hardenable compound includes a polyether group containing hardenable prepolymer as component (A) or part of component (A), that is, a prepolymer comprising a polyether group(s) and reactive moieties which upon addition of a suitable catalyst or initiator can react with each other and thus form a polymeric network.

The molecular weight (Mn) of the polyether group(s) containing prepolymer is typically in a range from about 150 to about 20,000 g/mol, or in the range from about 250 to about 10,000 g/mol, determined e.g. with GPC methods know to the person skilled in the art.

Suitable polyethers or polyether groups, which can be used, include those which meet the requirements in terms of material properties with regard to the preferred use as dental materials.

Appropriate polyethers or polyether groups can be produced in a manner known to the person skilled in the art by the reaction of the starting compound having a reactive hydrogen atom with alkylene oxides, for example ethylene oxide, propylene oxide, butylene oxide, styrene oxide, tetrahydrofurane or epichlorohydrine or mixtures of two or more thereof.

Especially suitable are polyether compounds which are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

The reaction products of low-molecular-weight polyfunctional alcohols having at least two hydroxyl groups with alkylene oxides, so-called polyethers, may also be used as polyols. The alkylene oxides preferably have from 2 to 4 carbon atoms. Suitable polyols are, for example, the reaction products of ethylene glycol, propylene glycol, butanediol or hexanediol isomers with one or more of the following alkylene oxides: ethylene oxide, propylene oxide or butylene oxides like tetrahydrofurane. Furthermore, the reaction products of polyfunctional alcohols such as glycerol, trimethylolethane or trimethylolpropane, pentaerythritol or sugar alcohols, or mixtures of two or more thereof, with the mentioned alkylene oxides, forming polyether polyols are also suitable.

Suitable starting compounds are, for example, water, ethylene glycol, 1,2- or 1,3-propylene glycol, 1,4- or 1,3-butylene glycol, 1,6-hexanediol, 1,8-octanediol, neopentyl glycol, 1,4-hydroxymethylcyclohexane, 2-methyl-1,3-propanediol, glycerol, trimethylolpropane, 1,2,6-hexanetriol, 1,2,4-butanetriol, trimethylolethane, pentaerythritol, mannitol, sorbitol, or mixtures of two or more thereof.

Especially suitable are polyether compounds as are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

For example, polyether polyols which are prepared by copolymerisation of tetrahydrofuran and ethylene oxide in a molar ratio of from 10:1 to 1:1, preferably to 4:1, in the presence of strong acids, for example boron fluoride etherates, are suitable.

The inventive composition comprises at least a component having at least 1 aziridine moiety or more, if desired, e.g. at least 2 or 3 or 4 or 5 or 6 aziridine moieties. Using a component with at least 2 azirdine moieties can be preferred to ensure a sufficient crosslinking.

According to another embodiment, the composition comprises on average at least 2 aziridine moieties.

The term "on average" is to be interpreted such in the context of the present text that a mixture of a large number of compounds may comprise both compounds having less than 2 aziridino groups and also compounds having more than 2 aziridine groups although, when seen over the entirety of the compounds of component (A), the average functionality of all molecules is, with respect to aziridine groups, 2 or more.

All mentioned types of polyaddition or polycondensation products can be provided with aziridine groups by means of any desired subsequent reactions known to the person skilled in the art. For example, it is possible first to introduce, into an appropriate polymer, substituents which are in turn capable of reacting with suitable aziridine derivatives.

It is also possible to polymerise cyclic ethers, preferably epoxides, onto the chain so that products are obtained which at the end contain substituents which can react with aziridine. There come into consideration, for example, polyethers onto which halo-substituted epoxides, e.g. epibromohydrin, are polymerised.

Suitable possible methods for providing the polymers with aziridine groups are mentioned, e.g., in U.S. Pat. No. 3,453,242.

Suitable polymers carry the aziridine groups terminally or laterally, or terminally and laterally, but preferably terminally.

The aziridine groups containing polymers typically have a dynamic viscosity η of from 10 to about 500 Pa*s, especially from about 15 to about 300 Pa*s. A preferred viscosity range is from about 20 to about 180 Pa*s at 23° C.

The aziridine equivalent is typically from about 250 to about 25,000 g/equivalent, especially from about 400 to about 10,000 g/equivalent. The term "aziridine equivalent" is defined as (molecular mass of the molecule)/(number of aziridine groups present in the molecule).

Using compounds having such an aziridine equivalent weight may facilitate the provision of rubber-like or elastomeric materials (after hardening). Compounds having an aziridine equivalent weight outside this range might either be too hard or brittle or too soft, e.g. do not have the desired Shore hardness or tensile strength.

The cationically hardenable compound which can be used may comprise only one type of aziridine group containing polymer. It is, however likewise possible for the cationically hardenable compound to comprise two or more different types of aziridine polymers, for example 3, 4 or 5 different types.

A "type of polymer" is understood, in the context of the present invention, to be a polymer as results from the polyaddition or polycondensation of selected monomers under the selected reaction conditions. A type of polymer can accordingly include polymer molecules of differing chemical constitution and differing molecular weight, depending on the reaction conditions selected. However, two reactions carried out using identical monomer compositions under identical reaction conditions always result, in accordance with the invention, in identical types of polymer. Two reactions which are carried out using identical monomers but under different reaction conditions may result in identical types of polymers but need not do so. The crucial factor therein is whether there are identifiable differences—in terms of chemical constitution, molecular weight and further parameters which can be determined—that are of relevance to the material properties. Two reactions which are carried out using different monomer compositions always result, in accordance with the invention, in different types of polymers.

Reactive side groups which pending from or attached to the backbone of the prepolymer include those characterized by the following formula (I)

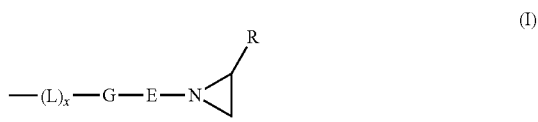

wherein

R represents H, C1-C12 alkyl, C2-C12 alkenyl, C2-C12 alkinyl, C7-C15 alkylaryl, C7-C15 arylalkyl, C3-C12 cycloalkyl, and wherein hydrogen atoms may be replaced by Cl or F and/or wherein up to five carbon atoms may be replaced by atoms or group of atoms selected from O, CO, N, S, E represents a C1-C18 branched or unbranched hydrocarbon chain wherein up to five carbon atoms may be replaced by atoms or group of atoms selected from O, CO, N, S, G represents a group selected from C(O)O, C(O)NR, C(O), C(O)C(O), C(O)(CH2)mC(O) with m=1 to 10, C(S)NR, CH2, L represents O, S, NR with x=0 or 1.

It can be preferred, if the prepolymer has a linear molecular structure. Thus, the prepolymer may typically comprise a linear backbone, which is typically end-capped with cationically hardenable moieties, including aziridine groups. Usually, there are no side chains, especially cationically hardenable side chains pending from the backbone.

The cationically hardenable compound is typically present in an amount of at least about 5 wt.-% or at least about 12 wt.-% or at least about 20 wt.-%.

The cationically hardenable compound is typically present up to an amount of about 95 wt.-% or up to about 80 wt.-% or up to about 75 wt.-%.

Typical ranges include from about 5 wt.-% to about 90 wt.-% or from about 12 wt.-% to about 80 wt.-% from about 25 wt.-% to about 70 wt.-%.

The cationically hardenable compound is typically present in an amount, which allows the formation of a sufficiently crosslinked network, in order to fulfil the practitioners needs.

By varying the amount of the cationically hardenable compound, e.g. the viscosity and the hardness of the cured composition can be adjusted.

If the amount of the cationically hardenable compound is too low, the resulting composition might not cure within the desirable period of time or might show not desirable mechanical properties.

If the amount of the cationically hardenable compound is too high, the resulting composition might be too viscous.

If desired, besides the cationically curable compound containing at least two aziridine groups, further curable compounds can be present being different from the cationically hardenable compound described above.

Thus, blends of various cationically polymerizable resins are also contemplated in this invention. Examples of such blends include two or more weight average molecular weight distributions of resin-containing compounds, such as low molecular weight (below 200), intermediate molecular weight (about 200 to 10,000) and higher molecular weight (above about 10,000).

Alternatively or additionally, the resin may contain a blend of resin-containing materials having different chemical natures, such as aliphatic and aromatic, or functionalities, such as polar and non-polar. Other cationically polymerizable polymers may additionally be incorporated, if desired.

If desired, the photopolymerizable composition can also contain a free-radically polymerizable material, including ethylenically unsaturated monomer, monomers or oligomers or polymers. Suitable materials contain at least one ethylenically unsaturated bond, and are capable of undergoing addition polymerization. Such free-radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]p-propoxyphenyldimethylmethane, and trishydroxyethylisocyanurate trimethacrylate; the bis-acrylates and bis-methacrylates of polyethylene glycols of molecular weight 200-500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

If desired, the polymerizable material(s) may contain both cationically polymerizable and free-radically polymerizable functionalities in a single molecule. These may be obtained, for example, by reacting a di- or poly-epoxide with one or more equivalents of an ethylenically unsaturated carboxylic acid. Examples of such materials include the reaction product of UVR-6105 (available from Union Carbide) or DER 332 (available from Dow Chemical Co.) with one equivalent of methacrylic acid. Commercially available materials having epoxy and free-radically polymerizable functionalities include the "Cyclomer" series, such as Cyclomer M100 or M101, available from Daicel Chemical, Japan.

The polymerizable material(s) can also contain hydroxyl and free-radically polymerizable functionalities in a single molecule. Examples of such materials include hydroxylalkylacrylates and hydroxyalkylmethacrylates such as hydroxyethylacrylate, hydroxyethylmethacrylate; glycerol mono- or di-acrylate and methacrylate; and the like.

The inventive composition also contains a radiation sensitive starter as component (B) or part of component (B) being able to start the hardening reaction of the cationically hardenable compound comprising at least one aziridine moiety.

The starter is typically able to produce cations (e.g. including $H^+$) when exposed to radiation. The radiation sensitive starter is sometimes characterized as a latent Lewis acid source.

According to one embodiment, the radiation sensitive starter can be characterized by at least one or more of the following features:
Molecular weight: being in a range from about 350 to about 2000 or from about 400 to about 1400,
Reduction potential E1/2red (On+) of the onium salt: at least about −1.1 Volt vs. SCE (Standard calomel electrode), or at least about −0.5 Volt vs. SCE or at least about −0.3 Volt vs. SCE.

Starters which were found to be useful are onium salts and ferrocenium salts as long as they are radiation sensitive.

In this respect it should be noted that not all onium salts are radiation sensitive. E.g. the sulfonium salts described in U.S. Pat. No. 4,167,618, US 2005/200585, US 2006/106127 are not radiation sensitive. Those salts do not generate reactive species upon exposure to radiation with a wavelength in the range from 250 to 1000 nm or within the spectrum visible to the human eye.

A particularly useful class of radiation sensitive starters include onium salts, especially iodonium salts or sulfonium containing low or non-coordinating anions.

Low or non-coordinating anions include $BF_4^-$, $PF_6^-$, $SbF_6^-$, $AsF_6^-$, $SbF_5OH^-$, $B(C_6F_5)_4^-$, $B(C_6(CF_3)_5)_4^-$, $B(C_6H_2(CF_3)_3)_4^-$.

Sulfonium salts which can be used include those bearing two or three aryl groups (including C1 to C8 substituted aryl and phenyl) attached to the sulfonium ion. Sulfonium salts, where the sulfonium ion bears an alkyl group are not useful, as those are typically not radiation sensitive.

Particularly, diaryliodonium salt(s) were found to be useful.

It can be advantageous, if the iodonium salt is soluble in the composition and preferably is shelf-stable, meaning it does not spontaneously promote polymerization when dissolved therein in the presence of the visible light sensitizer and the electron donor compound or without these additional components.

Accordingly, selection of a particular iodonium salt may depend to some extent upon the particular resin, and the optionally present visible light sensitizer and/or electron donor.

Suitable iodonium salts are described in U.S. Pat. Nos. 3,729,313, 3,741,769, 3,808,006, 4,250,053 and 4,394,403. The iodonium salt can be a simple salt, containing an anion such as $Cl^-$, $Br^-$, $I^-$ or $C_2H_5SO_3^-$; or a metal complex salt containing an antimonate, arsenate, phosphate or borate such as $SbF_5OH^-$ or $AsF_6^-$. Combinations of iodonium salts can be used if desired.

The diaryliodonium compounds may have the following structure (II):

[((R1)$_a$Ar1)—I—(Ar2(R2)$_b$)]$^+$Y$^-$ (II)

with Ar1 and Ar2 being independently of each other substituted or unsubstituted, fused or non-fused aromatic systems having 4 to 20 C atoms, including, for example, phenyl, tolyl, cumyl, anisyl, chlorophenyl, nitrophenyl, naphthyl, thienyl, furanyl and pyrazolyl, wherein R1 and R2 are identical or different and independently of each other denote an H atom, an aliphatic radical having 1 to 19, preferably 1 to 9 C atoms, it being possible for one or more C atoms to be replaced by O, C=O, O(C=O), F, Cl, Br, $SiR3_3$ and/or $NR3_2$ wherein $R^3$ is an aliphatic radical having 1 to 7 C atoms, in which one or more C atoms can be replaced by O, C=O and/or O(C=O), and a and b independently of each other can be 1 to 5. The aromatics Ar1 and Ar2 can be bonded to one another via R1 and/or R2.

The counter-anion $Y^-$ is typically an anion of low nucleophilicity having the following structure (III):

$$K_x L_y \quad\quad\quad (III)$$

wherein K is an element of main group III, V or VII, such as, for example, B, Al, P, Sb, As or I, and x can assume numerical values from 1 to 4, L independently of one another denotes aromatic, aliphatic, araliphatic or cycloaliphatic radicals having 1-25 C atoms, in which one or more C atoms can be replaced by F, Cl, Br or I, and y can assume numerical values from 0 to 6. Preferred radicals L are pentafluorophenyl, tetrafluorophenyl, trifluorophenyl, fluorophenyl, phenyl, 4-trifluoromethyl phenyl, 3,5-bis(trifluoromethyl)phenyl, 2,4,6-tris(trifluoromethyl)-phenyl, fluorine and iodine. Particularly preferred counter-ions $Y^-$ are $PF6^-$, $SbF6^-$ and $B(C_6F_5)_4^-$.

Examples of useful aromatic iodonium complex salt photoinitiators include: diphenyliodonium tetrafluoroborate; di(4-methylphenyl)iodonium tetrafluoroborate; phenyl-4-methylphenyliodonium tetrafluoroborate; di(4-heptylphenyl)iodonium tetrafluoroborate; di(3-nitrophenyl)-iodonium hexafluorophosphate; di(4-chlorophenyl)iodonium hexafluorophosphate; di(naphthyl)iodonium tetrafluoroborate; di(4-trifluoromethylphenyl)iodonium tetrafluoroborate; diphenyliodonium hexafluorophosphate; di(4-methylphenyl) iodonium hexafluorophosphate; diphenyliodonium hexafluoroarsenate; di(4-phenoxyphenyl)iodonium tetrafluoroborate; phenyl-2-thienyliodonium hexafluorophosphate; 3,5-dimethylpyrazolyl-4-phenyliodonium hexafluorophosphate; diphenyliodonium hexafluoroantimonate; 2,2'-diphenyliodonium tetrafluoroborate; di(2,4-dichlorophenyl) iodonium hexafluorophosphate; di(4-bromophenyl)-iodonium hexafluorophosphate; di(4-methoxyphenyl) iodonium hexafluorophosphate; di(3-carboxyphenyl) iodonium hexafluorophosphate; di(3-methoxycarbonylphenyl)iodonium hexafluorophosphate; di(3-methoxysulfonylphenyl)iodonium hexafluorophosphate; di(4-acetamidophenyl)iodonium hexafluorophosphate; di(2-benzothienyl)iodonium hexafluorophosphate; and diphenyliodonium hexafluoroantimonate.

Of the aromatic iodonium complex salts which are suitable for use in the compositions of the invention diaryliodonium hexafluorophosphate, diaryliodonium hexafluoroantimonate, 4-octyloxyphenyl phenyliodonium hexafluoroantimonate, 4-(2-hydroxytetradecyloxyphenyl)phenyliodonium hexafluoroantimonate, and 4-(1-methylethyl)phenyl 4-methylphenyliodonium tetrakis(pentafluorophenyl)borate are among the preferred salts. These salts are preferred because, in general, they promote faster reaction, and are more soluble in inert organic solvents than are other aromatic iodonium salts of complex ions.

The aromatic iodonium complex salts may be prepared by metathesis of corresponding aromatic iodonium simple salts (such as, for example, diphenyliodonium bisulfate). Thus, for example, the complex salt diphenyliodonium tetrafluoroborate can be prepared by the addition at 60° C. of an aqueous solution containing 29.2 g silver fluoroborate, 2 g fluoroboric acid, and 0.5 g phosphorous acid in about 30 ml of water to a solution of 44 g (139 millimoles) of diphenyliodonium chloride. The silver halide that precipitates is filtered off and the filtrate concentrated to yield diphenyliodonium fluoroborate which may be purified by recrystallization.

The aromatic iodonium simple salts may be prepared by various methods including (1) coupling of two aromatic compounds with iodyl sulfate in sulfuric acid, (2) coupling of two aromatic compounds with an iodate in acetic acid-acetic anhydride-sulfuric acid, (3) coupling of two aromatic compounds with an iodine acetate in the presence of an acid, and (4) condensation of an iodoso compound, an iodoso diacetate, or an iodoxy compound with another aromatic compound in the presence of an acid. Diphenyliodonium bisulfate is prepared by method (3), for example, by the addition over a period of eight hours at below 5° C. of a mixture of 35 ml of conc. sulfuric acid and 50 ml of acetic anhydride to a well-stirred mixture of 55.5 ml of benzene, 50 ml of acetic anhydride, and 53.5 g of potassium iodate. The mixture is stirred for an additional four hours at 0°-5° C. and at room temperature (about 25° C.) for 48 hours and treated with 300 ml of diethyl ether. On concentration, crude diphenyliodonium bisulfate precipitates and may be purified by recrystallization if desired.

Besides onium salts also ferrocenium salts were found to be useful.

Ferrocenium salts which can be used include those represented by the following formula:

$$[R^1{}_a(C_6H_n)Fe(C_5H_m)R^2{}_b]^+Y^-$$

with n=1, 2, 3, 4, 5; m=1, 2, 3, 4; a=1, 2, 3, 4, 5; b=1, 2, 3, 4; n+a=6; m+b=5;
$R^1$=H, C1 to C6 alkyl; $R^2$=H, C1 to C6 alkyl; Y=as defined above.

Specific examples for ferrocenium salts which can be used include eta-6-Cumol eta-5-cyclopentadienyl iron-hexafluorophosphate, eta-6-Cumol eta-5-cyclopentadienyl iron-hexafluoroantimonat, eta-6-Cumol eta-5-cyclopentadienyl iron-tetrafluorborat. Cumol or cumene has the formula $C_6H_5CH(CH_3)_2$.

The molar ratio between the starter and the cationically hardenable compound includes ranges from about 1.0:0.1 to about 1.0:20.0, or from about 1.0:0.5 to about 1.0:10.0, or from about 1.0:0.8 to about 1.0:30.

As the starter does not only act as a catalyst but chemically react—to a certain extend—with the hardenable composition, a sufficient amount of initiator should be present.

The amount of the starter to be used is not particularly limited, unless the desired curing reaction cannot be achieved.

The starter is typically present in an amount of at least about 0.1 wt.-% or at least about 0.5 wt.-%.

The starter is typically present up to an amount of about 50 or up to about 35 wt.-% or up to about 20 wt.-%.

Typical ranges for the starter include from about 0.25 wt.-% to about 50 wt.-% or from about 0.5 wt.-% to about 40 wt.-% from about 1 wt.-% to about 25 wt.-%, wt.-% with respect to the weight of the whole composition.

If the amount of the starter is too low, the desired depth of cure may not be obtained.

Besides radiation sensitive starters, the composition can also comprise other starters as well, e.g. starters which have already been used for curing aziridine moieties containing compositions.

Adding a further initiator might be beneficial for improving or enhancing the depth of cure.

These starters are typically Lewis acids. Useful initiators are e.g. sulfonium salts, especially alkyl sulfonium salts or sulfonium salts derived from glutaconic acid. Those and others are described e.g. in WO 2007/016295 or U.S. Pat. No. 4,167,618, the content of which in regard to initiators is explicitly mentioned and herewith incorporated by reference.

This initiator can be used in an amount of at least about 1 wt.-% or at least about 2 wt.-% or at least about 3 wt.-% with respect to the whole composition.

The initiator can be used up to an amount of at least about 30 wt.-% or at least about 20 wt.-% or at least about 10 wt.-% with respect to the whole composition.

It can be beneficial, if the cationically curable composition can be cured by using visible light, that is, with radiation having a wavelength in the range from about 380 to about 800 nm or from about 400 to about 500 nm.

In this case, it is recommended that a sensitizer, especially a visible light sensitizer is present, as component (C) or part of component (C).

A "sensitizer" is defined as a compound or a combination of compounds which are able to absorb the radiation in the emitted wavelength or in a region of the emitted wavelength and to generate the initiating species of the polymerization reaction.

According to one embodiment, the sensitizer may have a molecular weight: being in a range from about 50 to about 1000 or from about 100 to about 800.

The sensitizer should be partly, essentially or completely soluble in the photopolymerizable composition, free of functionalities that would substantially interfere with the cationic polymerization process, and capable of light absorption somewhere within the range of wavelengths between about 400 and about 1000 nanometers (nm). Preferred visible light sensitizers contain one or more carbonyl functional groups.

Suitable visible light sensitizers may include compounds in the following categories: ketones, coumarin dyes (e.g., ketocoumarins), xanthene dyes, fluorone dyes, fluorescein dyes, aminoketone dyes, and p-substituted aminostyryl ketone compounds. Ketones (e.g., monoketones or alpha-diketones), coumarin dyes (e.g., ketocoumarins), xanthene dyes, fluorone dyes, and fluorescein dyes are particularly preferred visible light sensitizers for use in the invention. For applications requiring deep cure, it is preferred to employ sensitizers having an extinction coefficient below about 1000 lmole$^{-1}$cm$^{-1}$, more preferably about or below 100 lmole$^{-1}$cm$^{-1}$, at the desired wavelength of irradiation for photopolymerization.

The alpha-diketones are an example of a class of visible light sensitizers having this property, and are particularly preferred for dental applications.

By way of example, a preferred class of ketone visible light sensitizers has the formula (IV):

ACO(X)$_b$B     (IV)

where X is CO or CR$^1$R$^2$ where R$^1$ and R$^2$ can be the same or different, and can be hydrogen, alkyl, alkaryl or aralkyl, b is zero, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable I-diketones (b=1 and x=CO) include 2,3-butanedione, 2,3-pentanedione, 2,3-hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, 1-phenyl-1,2-propanedione, and the like.

Examples of particularly preferred visible light sensitizers include the alpha-diketones: camphorquinone; glyoxal; biacetyl; 3,3,6,6-tetramethylcyclohexanedione; 3,3,7,7-tetramethyl-1,2-cycloheptanedione; 3,3,8,8-tetramethyl-1,2-cyclooctanedione; 3,3,18,18-tetramethyl-1,2-cyclooctadecanedione; dipivaloyl; benzil; furil; hydroxybenzil; 2,3-butanedione; 2,3-pentanedione; 2,3-hexanedione; 3,4-hexanedione; 2,3-heptanedione; 3,4-heptanedione; 2,3-octanedione; 4,5-octanedione; 1,2-cyclohexanedione; and 1-phenyl-1,2-propanedione. Of these, camphorquinone is the most preferred visible light sensitizer.

Examples of preferred fluorone dyes include, but are not limited to, fluorescein, 4'5'-dibromofluorescein, erythrosin B, ethyl eosin, eosin Y, and erythrosin, yellowish blend.

The molar ratio between the sensitizer and the starter includes ranges from about 1.0:0.1 to about 1.0:20.0, or from about 1.0:0.5 to about 1.0:10.0, or from about 1.0:0.8 to about 1.0:30.

The amount of the sensitizer to be used is not particularly limited, unless the desired curing reaction cannot be achieved.

If present, the sensitizer is typically present in an amount of at least about 0.1 wt.-% or at least about 0.5 wt.-%.

The sensitizer can be present up to an amount of about 50 or up to about 35 wt.-% or up to about 20 wt.-%.

Typical ranges for the sensitizer include from about 0.025 wt.-% to about 50 wt.-% or from about 0.05 wt.-% to about 40 wt.-% from about 0.1 wt.-% to about 25 wt.-%, wt.-% with respect to the weight of the whole composition.

If the amount of the sensitizer is too low, the desired physical properties (e.g. depth of cure) may not be obtained.

If the amount of the sensitizer is too high, the resulting composition might become too expensive from an economically point of view.

The initiator system used for hardening the composition may also comprise an electron donor compound as component (D) or part of component (D).

Adding an electron donor compound can be beneficial, if the hardenable composition should be hardened using visible light.

A wide variety of electron donor compounds can be employed, and generally are capable of increasing the speed of polymerization and/or the depth of polymerization of the inventive composition when exposed to visible light of the desired wavelength, as compared to the same composition but excluding the electron donor compound.

Preferred electron donor compounds possess one or more (and more preferably several if not all) of the following properties:

(a) they are at least partly soluble in a polymerizable or hardenable composition;
(b) they do not absorb a significant amount of light at the wavelength of the light used to photopolymerize the composition, typically the wavelength at which the visible light sensitizer exhibits maximum absorption, by which it is meant that the electron donor compound does not detrimentally affect the performance of the visible light sensitizer;
(c) they have an oxidation potential (E$_{ox}$) greater than 0 but less than that of 1,4-dimethoxybenzene when measured versus a saturated calomel electrode (SCE);

(d) they yield a photoinitiator system that has a photoinduced potential less than that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone;

(e) they impart not more than a minimal amount of objectionable colour to the polymerized resin;

(f) they can be used in a lower effective concentration than other polymerization aids. Other factors that may influence the selection of the electron donor compound for a particular composition include the cationically polymerizable resin, the iodonium salt, and the visible light sensitizer that have been chosen, as well as the shelf stability of the cationically polymerizable composition.

A wide variety of electron donor compounds can be used including biphenylene(s), anthracene(s), aromatic tertiary amine(s), aromatic ether(s), mixtures, derivatives and combinations thereof.

One class of electron donor compounds which can be used are compounds containing a biphenylene structure, including biphenylenes bearing alkyl groups.

In a preferred embodiment the alkyl groups pending on the biphenylene ring structure are arranged symmetrically.

The alkyl substituents are preferably at the positions 2, 3, 6, and 7. In a further embodiment there are not more than 2 substituents at the positions 2 and 6 or 2 and 7. Preferably, the alkyl substituents are independently selected from methyl groups or tert-butyl groups. The biphenylene structure typically does not comprise alkoxy groups like e.g. methoxy groups, being directly attached onto the biphenylene structure.

More specifically, electron donor compounds comprising the structure (V) shown below may be employed.

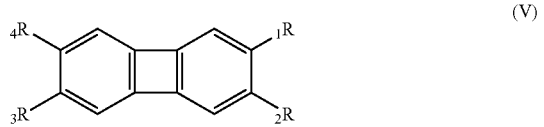

wherein each of $R_1$ to $R_4$ is independently selected from H, or alkyl groups, wherein the R-group substituents may also cooperate to form a cycloalkyl ring. Preferred R-group substituents include methyl, ethyl, iso-propy, n-propyl, and tert-butyl groups, with the methyl and tert-butyl groups being most preferred.

More specifically, according to a preferred embodiment the electron donor compound of the invention can be characterized by at least one of the following features:

a. The biphenylene compound bears at least one, two or three but not more than about four alkyl (e.g. C1 to C4) groups.
b. The substituted biphenylene compound is symmetric (reflection and/or rotation).
c. The biphenylene compound does not contain alkoxy groups directly attached onto the biphenylene structure.
d. The biphenylene compound has a molecular weight in the range of about 180 to about 380.

The combination of features a, c and d or b, c and d can be preferred.

Another class of electron donor compounds which can be used are compounds containing an anthracene structure.

The anthracene may be, for example, an unsubstituted anthracene or an alkyl or alkoxy substituted anthracene, such as 2-ethyl-9,10-dimethoxyanthracene (EDMOA), 2,6-di-tert-butylanthracene, 9,10-diethoxyanthracene, 1,4-dimethoxyanthracene or 9,10-dimethylanthracene. If desired, mixtures of anthracenes can be used.

In another embodiment, a combination of two or more substituted anthracenes, wherein one of the anthracenes is an alkoxy substituted anthracene (e.g., EDMOA) and the other anthracene is an alkyl, phenyl or alkoxy substituted anthracene.

It is also possible to use alone or in combination anthacenes comprising the structure (VI)

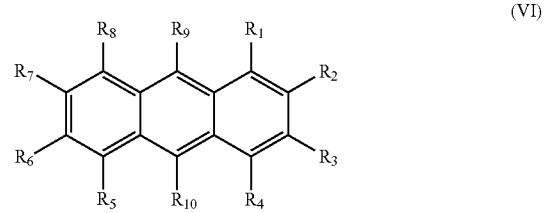

wherein each of R1 to R10 is independently selected from H, alkyl (e.g. C1 to C10), phenyl or alkoxy groups (e.g. C1 to C10), provided that at least one of R1 to R10 is not H.

Preferred R-group substituents are methyl, ethyl, propyl, butyl, tert-butyl, methoxy, and ethoxy.

Particularly useful anthracene-based compounds include: 2-ethyl-9,10-dimethoxyanthracene (EDMOA), 9,10-dimethylanthracene, 9,10-diethoxyanthracene, 1,4-dimethoxyanthracene, 9-methylanthracene, 2-ethylanthracene, 2-tert-butylanthracene, 2,6-di-tert-butylanthracene, 9,10-diphenyl-2,6-di-tert-butylanthracene, 1-amino anthracene, 2-amino anthracene and combinations thereof. All of these compounds with the exception of the 2,6-di-tert-butylanthracene derivatives are available from Sigma-Aldrich, St. Louis, Mo.

Another class of electron donor compounds which can be used are compounds containing an aromatic tertiary amine structure as e.g. described in U.S. Pat. No. 6,084,004 and/or U.S. Pat. No. 6,043,295: (which is herewith incorporated by reference):

with $R^1$, $R^2$ and $R^3$ being identical or different and independently of one another selected from H, an aliphatic, aromatic or araliphatic radical having 1 to 19 or 1 to 7 carbon atoms, it being possible for one or more carbon atoms to be relaced by O, C=O, —O(C=O)—, wherein $R^1$ and $R^2$ together can from ring structures which are unsubstituted or substituted by aliphatic (C1-C19), cycloaliphatic, (C1-C20) heteroaromatic or fused aromatic radicals.

Typical examples include dimethylaniline, diethylaniline, 4-dimethylaminobenzoic acid, ethyl 4-dimethylaminobenzoate, 3-dimethylaminobenzoic acid, 4-dimethylaminobenzoin, 4-dimethylaminobenzaldehyde, and 4-dimethylaminobenzonitrile.

Another class of electron donor compounds which can be used are aryl alkyl polyether(s). Useful compounds can be characterized by the following formula:

with n being 1 to 3, and $R^3$ and $R^4$ being independently H or $C_{1-18}$ alkyl that is optionally substituted by one or more halogen, —CN, —OH, —SH, $C_{1-18}$ alkoxy, $C_{1-18}$ alkylhio, $C_{3-18}$ cycloalkyl, aryl, substituted aryl, —COOH, $COOC_{1-18}$ alkyl.

Typical examples include those mentioned in U.S. Pat. No. 6,043,295 (which is herewith incorporated by reference) and in particular 1,2,4-trimethyloxybenzene.

The amount of the electron donor compound which can be used is not particularly limited, unless the desired curing reaction cannot be achieved.

If present, the electron donor compound is typically present in an amount of at least about 0.025 wt.-% or at least about 0.05 wt.-%.

The electron donor compound can be present up to an amount of about 50 or up to about 35 wt.-% or up to about 20 wt.-%.

Typical ranges for the electron donor compound include from about 0.025 wt.-% to about 50 wt.-% or from about 0.05 wt.-% to about 40 wt.-% from about 0.1 wt.-% to about 25 wt.-%, wt.-% with respect to the weight of the whole composition.

If the amount of the electron donor compound is too low, the desired physical properties may not be obtained.

If the amount of the electron donor compound is too high, the resulting composition might not yield the desired rate of polymerization.

The inventive dental composition may comprise a filler matrix as component (E) or part of component (E). The filler matrix can be comprised of one filler or a mixture of different fillers.

The nature of filler of the inventive composition is not particularly limited. The size of the filler particles should be such that a homogeneous mixture with the hardenable component(s) forming the resin matrix can be obtained.

The BET surface of the filler is typically in a range from about 0.05 to about 50 m$^2$/g or from about 0.5 to about 30 m$^2$/g or from about 0.5 to about 20 m$^2$/g. Using a filler with a BET surface within this range can be beneficial to adjust the viscosity and tensile strength.

If desired, the BET surface of the filler can be determined as described in DIN 66132. Alternatively, the values for the BET surface are taken from a material data sheet provided by the supplier.

The size of the filler particles should be such that a homogeneous mixture can be obtained. The particle distribution is preferably chosen such that there are no fillers with particle sizes of more than 200 μm.

Typically, the size of the filler particles (d50 value) is below about 40 μm or below about 10 μm or below about 5 μm. Typical ranges (d50 value) include from about 0.1 to about 40 μm or from about 0.5 to about 20 μm or from about 1 to about 10 μm.

The mean particle size, if desired, can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

The term d50/μm with regard to particle size measurement means that in 50% of the analyzed volume, the particles have a size below x μm. E.g., a particle size value of below 100 μm (d50/μm) means that within the analyzed volume, 50% of the particles have a size below 100 μm.

If the filler particles are too small, the viscosity of the resulting composition might increase to a not desirable limit.

If the filler particles are too big, the detail accuracy might be negatively affected.

The filler comprises typically a filler body and a filler surface. The filler is typically in particle form.

The filler body typically comprises, consists essentially of or consists of SiO$_2$ moieties. Typical examples include quartz, cristobalite and silicates (e.g. components comprising anions of the formula [SiO$_3^{2-}$]$_n$, or [Si$_2$O$_5^{2-}$]$_n$) like wollastonite, nephelinsyenite, kaolin, talcum, feldspar, and mixtures and combinations thereof, wherein quartz and cristobalite are sometimes preferred.

The surface of this filler may comprise side groups with polar moieties.

By "side group" it is meant that the polar moiety is not directly attached to the filler body (e.g. like Si—OH moieties being present on the surface of a quartz filler), but that the polar moiety is linked to the surface of the filler body by a spacer group.

"Polar moieties" are defined as chemical groups having a dipole moment. Examples of such chemical groups include ethers, alcohols, thiols, phosphines, amines (prim., sec., tert.), amide, urethanes, esters, oxiranes, oxetanes, hydrated furanes, thiiranes and combinations thereof.

Side groups with polar moieties can be attached to the filler surface by applying the following steps: dispersing the filler in a solvent, adjustment of the pH, adding of a silane coupling agent, heat treatment, removal of solvent, drying of the filler, solvent exchange process, milling of the filler.

Silane coupling agents, which can be used for the surface-treatment of the filler include substances which can be characterized by formula (IX):

$$E\text{-}F\text{-}G \quad\quad\quad (IX)$$

wherein E comprises a polar moiety (as described above), F comprises Si, and G comprises at least one hydrolysable group.

By "hydrolysable group" is meant a group, which can react e.g. with OH-groups being present on the surface of the filler.

Examples of hydrolysable groups include halogens (e.g. F, Cl and Br), pseudo-halogens (e.g. azides) and alcoholates (e.g. C1-C6, alkyl and aryl).

More specifically, silane coupling agent which can be used include those which can be characterized by formula (X)

$$A_m\text{-}B\text{—}Si(R^1)_n(OR^2)_{3-n} \quad\quad\quad (X)$$

with A comprising a polar moiety (including —O—, —S—, —NH—, —OH, —SH, —CO—, —CO—O—, —CO—NH—and combinations thereof, wherein moieties comprising amines, oxiranes, and combinations thereof are preferred, B comprising a spacer group, such as (i) linear or branched C1 to C12 alkyl, (ii) C6 to C12 aryl, (iii) organic group having 2 to 20 carbon atoms bonded to one another by one or more ether, thioether, ester, thioester, thiocarbonyl, amide, urethane, carbonyl and/or sulfonyl linkages, R$^1$ comprising an alkyl group (e.g. C1 to C6) or an aryl group (e.g. C6 to C12), and R$^2$ comprising an alkyl group (e.g. C1 to C6), with m=1, 2, 3 or 4 and n=0, 1 or 2.

Non-polar moieties are e.g. —Si—OR, —Si—O—Si—, —Si—R, with R being alkyl (e.g. C1 to C6) or aryl (e.g. C1 to C6). These kinds of moieties do not show a sufficient dipole moment.

Preferably, the surface of the filler should not contain or be essentially free of acidic groups like —COOH and —SO$_3$H.

The pH value of a 10 wt.-% dispersion of the filler in water is typically within the range from about 7 to about 12. Using a filler having a pH value within this range can be beneficial to improve the storage stability and shelf life of the composition.

The pH value can be determined with means known to the person skilled in the art.

The following commercially available fillers were found to be particularly useful: quartz comprising amino-silane groups (e.g. Silbond™ 600 AST, Silbond™ 800 AST; Quarzwerke Frechen), wollastonite comprising amino-silane groups (e.g. Tremin™ 283-600 AST or Tremin™ 939-300 AST; Quarzwerke Frechen), quartz/kaolin mixture comprising amino-silane groups (e.g. Aktisil™ AM; Quarzwerke Frechen), quartz comprising epoxy groups (e.g. Silbond™ 600 EST, Silbond™ 800 EST; Quarzwerke Frechen) and quartz comprising trimethyl-silane groups (e.g. Silbond™ 800 RST).

Besides surface-treated fillers, non-surface treated fillers can be added. A "non-surface treated filler" in the context of the invention is a filler having a surface which has not been exposed to reactive substances resulting in a modification of the surface of the filler to make the filler more compatible with other components of the composition.

A wide variety of inorganic, hydrophilic or hydrophobic fillers may be employed such as silicas, aluminas, magnesias, titanias, inorganic salts, metallic oxides, quartz, cristobalit, kaolin, talcum, feldspar, wollastonit, nephelinsyenit, silicates and glasses. It has been found to be possible to employ mixtures of silicone dioxides, such as a diatomaceous earth and/or fumed silica. Those filler are commercially available from companies like Cabot Corporation, Wacker or Degussa under the trade names Aerosil™ (Degussa) HDK-H, HDK 2050 (Wacker), Cab-o-Sil (Cabot), Celatom W25 (Chemag).

More specifically, fillers which can be used include calcium silicate, diatomaceous earth, zirconium silicate, montmorillonite such as bentonite, zeolite, including molecular sieves such as sodium aluminium silicate, barium sulphate, calcium carbonate, plaster, glass and plastic powder.

The sizes and surface areas of the foregoing materials can be adjusted to control the viscosity and thixotropicity of the resulting compositions.

A combination of reinforcing and non-reinforcing fillers sometimes even further improves the rheology of the uncured composition and the elasticity of the cured composition.

Typical reinforcing fillers include fumed silica, carbon black and the like. They also can improve mechanical properties like tensile strength or tear strength, of the cured silicone composition.

Typical non-reinforcing fillers include precipitated silicas, diatomaceous earth, aluminas, magnesias, titanium dioxide, zirconium silicate and mixtures and combinations thereof.

There is no need for a filler to be present at all. If, however, a filler is present, the filler is present in an amount of at least about 1 wt.-% or at least about 5 wt.-% or at least about 10 wt.-% with respect to the whole composition.

There is no particular upper limit, however, typically the amount of filler, if present at all, is used in an amount of at most about 80 wt.-% or at most about 75 wt.-% or at most about 70 wt.-% with respect to the whole composition.

Thus, typical ranges for the filler include from about 10 to about 80 or from about 15 to about 75 or from about 20 to about 70 wt.-% with respect to the whole composition.

If the amount of the filler is too low, a desired Shore hardness might not be obtained.

If the amount of the filler is too high, the elasticity of the cured composition might negatively be affected and the viscosity of the un-cured composition might be too high. Moreover, the shelf life might negatively be influenced.

According to a further embodiment, the composition can also comprise one or more additives as component (F) or part of component (F).

The compositions of the invention can also contain suitable adjuvants such as accelerators, inhibitors or retarders, absorbers, stabilizers, pigments, dyes, viscosity modifiers, surfactants and wetting aids, antioxidants, and other ingredients well known to those skilled in the art.

The amounts and types of each ingredient in the composition should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

Typical adjuvants include pigments, colorants and/or dyes. Examples include titanium dioxide or zinc sulphide (lithopones), red iron oxide 3395, Bayferrox 920 Z Yellow, Neazopon Blue 807 (copper phthalocyanine-based dye) or Helio Fast Yellow ER.

Accelerators, which can be used include components having a bi- or polycyclic aromatic amine structure, especially a bi- or polycyclic aromatic tert. amine or a bi- or polycyclic aromatic like N,N-dialkyl (e.g. C1 to C12 or C1 to C6) amine. Specific examples include 1,8-bis(N,N-dimethylamino)-naphthaline and N,N-dimethyl-1-naphthylamine.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)-methylphenol, 4-methoxybenzylalcohol, 2,6-di-tert.-butyl-4-methylphenol ("Jonol"), 3-methoxyphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzo-phenone (UV-9), 2-(2'-hydroxy-4',6'-di-tert-pentylphenyl)-2H-benzotriazole, 2-hydroxy-4-n-octoxybenzophenone, 2-(2'-hydroxy-5'-methacryloxyethylphenyl)-2H-benzotriazole, phenothiazine, tocopherol, polyethylene imine, substituted pyridines (e.g. 2,6-di-tert.-butyl-4-methylpyridine) and HALS (hindered amine light stabilizers). Such adjuvants may optionally comprise reactive functionality so that they will be copolymerized with the resin.

All kinds of known and compatible softeners and rheology modifiers like non reactive polymeric fluids or fats commonly used in commercialized impression materials can be added Preferred are those ingredients and additives that do not add unpleasant smell or taste. Compounds that have an unpleasant smell might be removed by thinfilm evaporation, if needed.

Typical plasticisers include, e.g., compounds of the ester type such as C12- to C15-alkyl lactates, ethyl or butyl esters of citric acid or of acetylcitric acid, phthalic acid esters of relatively long, branched alcohols such as bis(2-ethylhexyl) phthalate or phthalic acid polyester, C2- to C22-dialkyl esters of C2- to C6-dicarboxylic acids such as bis(2-ethylhexyl) adipate, dioctyl maleate, diisopropyl adipate, aromatic and aliphatic sulfonic acid esters such as C2- to C20-alkylsulfonic acid esters of phenol or of C1- to C22-alkanols or typical aromatic plasticisers such as polyphenyls in a wide viscosity range, including wax-like polyphenyls such as are obtainable, for example, from the Monsanto company, isomeric mixtures of C20 to C40 aromatic compounds, with preference being given to the use of mixtures of plasticisers of the ester type and aromatic type.

Liquids such as C12-C15 alkyl acetates, liquid derivatives of citric acid, esters of phthalic acid with branched alcohols like bis(2-ethylhexyl)phthalate or polymeric phthalates, C2-C18 bis(alkyl)esters of C2-C6 dicarboxylic acids like dioctylmaleate, dioctyladipate, aromatic and aliphatic esters of sulfonic acids like Mesamoll™, aromatic and aliphatic amides of sulfonic acides like N-ethyl toluene solfonic acid amide or N-butyl benzene sulfonic acid amide, typical aromatic diluters like poly phenyls, xylyl toluene, and dixylyl toluene can be used. Also low molecular weight alcohols that may contain more than one OH-function like propane-1,2-diol may be used. From the group of polymeric compounds, polypropylene glycols and its derivatives are sometimes preferred.

Suitable diluting agent(s) usually do not contain reactive moieties like —SH or —COOH, primary or secondary amino groups, but may contain —OH. Liquids such as $C_{12}$-$C_{15}$ alkyl acetates, liquid derivatives of citric acid, esters of phthalic acid with branched alcohols like bis(2-ethylhexyl)phthalate or polymeric phthalates, $C_2$-$C_{18}$ bis(alkyl)esters of $C_2$-$C_6$ dicarboxylic acids like dioctylmaleate, dioctyladipate, aromatic and aliphatic esters of sulfonic acids like Mesamoll™, aromatic and aliphatic amides of sulfonic acides like N-ethyl toluene solfonic acid amide or N-butyl benzene solfonic acid amide, typical aromatic diluters like poly phenyls, dibenzyl toluene, xylyl toluene, dixylyl toluene and polymeric compounds like polyethers, polyesters, polycarbonates, polytetrahydrofuranes, polyolefines can be used. Also low molecular weight alcohols that may contain more than one OH-function like propane-1,2, diol or carbonates like propylene carbonate may be used. From the group of polymeric compounds, polypropylene glycols and its derivatives are preferred.

The composition typically does not contain water, especially added water. However, small amounts of water (e.g. below about 3 wt.-% or below about 1 wt.-%) might be present due to the natural water content of the individual components of the formulation.

An example of a preferred plasticiser combination is a mixture of acetyl tributyl citrate and dibenzyltoluene.

Likewise suitable as additives are triacyl esters of glycerol of non-animal origin. Suitable additives can consist of, for example, modified fats of vegetable origin such as hydrogenated palm oil or soybean oil or synthetic fats.

Suitable fats are described in U.S. Pat. No. 6,395,801, to the full content of which reference is here made. Avocado oil, cottonseed oil, groundnut oil, cocoa butter, pumpkin seed oil, linseed oil, maize germ oil, olive oil, palm oil, rice oil, rapeseed oils, safflower oil, sesame oil, soybean oil, sunflower oil, grapeseed oil, wheat germ oil, Borneo tallow, fulwa butter, hemp oil, MO butter, lupin oils, candlenut oil, kapok oil, katiau fat, kenaf seed oil, kekuna oil, poppy seed oil, mowrah butter, okra oil, perilla oil, sal butter, shea butter and tung oil are especially suitable, provided that the fats in question have been hydrogenated before use. Suitable hydrogenated fats are considered to be those whose iodine value is less than 20 (measured in accordance with the DGF [German Society for Fat Science] standard C-V 11 Z2). Fat hydrogenation procedures are described, for example, in "Ullmanns Enzyklopädie der industriellen Chemie", 4th edition, volume 11, p. 469.

Mixtures of naturally occurring fats, and also synthetically prepared fats such as Softisan™ 154 or Dynasan™ 118 (from Hüls Comp.) can likewise be used. The preparation of such synthetic triacyl glycerides is relatively simple for the person skilled in the art and can be carried out by starting from glycerol and the appropriate fatty acid methyl esters. Such esterification reactions are described in, inter alia, "Houben-Weyl, Methoden der Organischen Chemie", Vol. E5/Part 1, p. 659 ff.

Preferred triacyl glycerides correspond to the formula (XI):

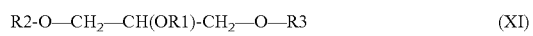

(XI)

in which R1, R2 and R3 denote, each independently of the others, $C_{11}H_{23}CO$, $C_{13}H_{27}CO$, $C_{15}H_{31}CO$ or $C_{17}H_{35}CO$. Mixtures of such triacyl glycerides can also be used.

Suitable thixotropic agent(s) which can be added to the composition of the invention are organic compounds e.g. waxes according to the definition in Ullmanns Enzyklopädie der technischen Chemie, 4. Auflage, Verlag Chemie, Weinheim, Band 24, page 3 or triglycerides as described in U.S. Pat. No. 6,127,449. In general all organic non-water based thixotropic agents are suitable. That means that suitable thixotropic agents can alter the rheology especially of non-water based formulation.

The curable composition may also include one or more surfactant(s), especially Si-containing surfactant(s) or mixture of Si-containing surfactants.

If surfactant(s) are present they are typically present in an amount sufficient and not detrimental to the desired effect or effects to be achieved.

Surfactants or hydrophilizing agents which can be employed can generally be chosen freely from all types of surfactants which improve the hydrophilicity of a polyether group containing polymer.

Preferably, the use of the surfactant should not negatively impact the material properties or curing behavior of the curable composition or at least not more than avoidable or tolerable.

Surfactant(s) can comprise an agent or a plurality of agents which are generally capable of increasing the hydrophilic character to a composition, for example as demonstrated by a decrease in the wetting angle of a drop of water or an aqueous solution or dispersion (e.g. a plaster suspension or the like) on the material (in its cured or uncured state).

In certain embodiments, the surfactant does not contain reactive groups so that it is not incorporated into the network of the hardenable composition.

Useful surfactants also include polyether carbosilanes of the general formula (XII)

(XII)

in which Q stands for $R_3Si$— or $R_3Si$—$(R'$—$SiR_2)_a$—$R'$—$SiR''_2$—, where every R in the molecule can be the same or different and stands for an aliphatic C1-C18, a cycloaliphatic C6-C12 or an aromatic C6-C12 hydrocarbon radical, which can optionally be substituted by halogen atoms, R' is a C1-C14 alkylene group, R" is R in the case of a≠0 or is R or $R_3SiR'$ in the case of a=0, and a=0-2; P stands for a C2-C18 alkylene group, preferably a C2-C14 alkylene group or A-R''', where A represents a C2-C18 alkylene group and R''' a functional group selected from: —NHC(O)—, —NHC(O)—(CH$_2$)$_{n-1}$—, —NHC(O)C(O)—, —NHC(O)(CH$_2$)$_v$C(O)—, —OC(O)—, —OC(O)—(CH$_2$)$_{n-1}$—, —OC(O)C(O)—, —OC(O)(CH$_2$)$_v$C(O)—, —OCH$_2$CH(OH)CH$_2$OC(O)(CH$_2$)$_{n-1}$—, —OCH$_2$CH(OH)CH$_2$OC(O)(CH$_2$)$_v$C(O)— with v=1-12; Z is H or stands for a C1-C4 alkyl radical or a C1-C4 acyl radical; x stands for a number from 1 to 200 and n stands for an average number from 1 to 6, preferably 1 to 4. Thus, the element —SiR"$_2$— can also comprise the substructure —Si(R)(R$_3$SiR')—.

Other surfactants which can be used, either alone or as a mixture of two or more thereof, can be found in U.S. Pat. No. 4,657,959 (Bryan et al.), col. 4, I. 46 to col. 6. I. 52 as well as in EP 0 231 420 B1 (Gribi et al.; also published as AU 6,857,087) p4, I. 1 to p. 5, I. 16 and in the examples.

U.S. Pat. Nos. 5,750,589, 4,657,959 and EP 0 231 420 B1 are expressly described and cited herein as a source of disclosure for compounds which can be used as component (E1) according to the invention.

Some of the surfactants, which can be used as component (E1) or part of component (E1) can be summarized under the following formula (XIII)

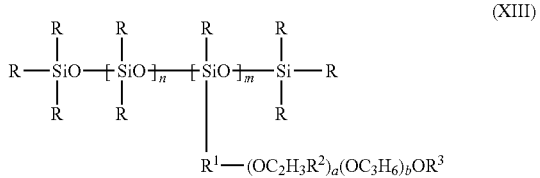

where each R is independently a monovalent hydrocarbyl radical with 1 to 22 C-atoms, $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and $R^3$ are —$CH_3$, $R^1$ is —$C_3H_6$—, $R^2$ is hydrogen, n is about zero or about one, m is about one to about five, a is about five to about 20 and b is about 0.

Several of such ethoxylated surfactants are for example available from Momentive Performance Materials Inc. including "SILWET™" surface active copolymers. Preferred surface active copolymers include Silwet 35, Silwet L-77, Silwet L-7600 and Silwet L-7602, Silwet L-7608 and Silwet Hydrostable 68 and Silwet Hydrostable 611. Silwet L-77 is an especially preferred ethoxylated surfactant which is believed to correspond to the above formula where R and $R^3$ are —$CH_3$, $R^1$ is —$C_3H_6$—, $R^2$ is hydrogen, n is about zero or about one, m is about one or about two, a is about seven, and b is about 0. Also possible is the use of MASIL™ SF19, as obtainable from Lubrizol performance products, Spartanburg, US.

Examples of useful non-ionic surfactants include those according to the formula (XIV):

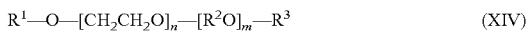

wherein $R^1$ represents hydrogen or an aromatic or aliphatic, linear or branched hydrocarbon group having 1-20 carbon atoms, $R^2$ represents an alkylene having 3 carbon atoms, $R^3$ represents hydrogen or a C1-C3 alkyl group, n has a value of 0 to 40, m has a value of 0 to 40 and the sum of n+m being at least 2.

It will be understood that in the above formula, the units indexed by n and m may appear as blocks or they may be present in an alternating or random configuration. Examples of non-ionic surfactants according to the formula above include alkylphenol oxethylates such as ethoxylated p-isooctylphenol commercially available under the brand name TRITON™ such as for example TRITON™ X 100 wherein the number of ethoxy units is about 10 or TRITON™ X 114 wherein the number of ethoxy units is about 7 to 8.

Still further examples include those in which $R^1$ in the above formula represents an alkyl group of 4 to 20 carbon atoms, m is 0 and $R^3$ is hydrogen. An example thereof includes isotridecanol ethoxylated with about 8 ethoxy groups and which is commercially available as GENAPOL™ X080 from Clariant GmbH.

Non-ionic surfactants according to the above formula with $R^1$ and $R^3$ representing a C1-C3 alkyl chain or hydrogen and in which the hydrophilic part comprises a block-copolymer of ethoxy groups and propoxy groups may be used as well. Such non-ionic surfactants are commercially available from Clariant GmbH under the trade designation GENAPOL™ PF 40 and GENAPOL™ PF 80. Further suitable non-ionic surfactants that are commercially available include Tergitol™ TMN 6, Tergitol™ TMN 10, or Tergitol™ TMN 100X. Also statistical, alternating or block copolymers of ethylene oxide and propylene oxide are suitable surfactants according to the present invention. Such non-ionic surfactants are available e.g. under the trade name Breox™ A, Synperonic™ or Pluronic™.

The inventive composition may also comprise in addition to other ingredients and surfactants, alone or in combination an F-containing component including those described in EP application number 09162681.2, especially those described on pages 21 to 27.

There is no need for additive(s) to be present, however, if additive(s) are present, they are typically present in an amount of at least about 0 wt.-% or at least about 0.005 wt.-% or at least about 0.01 wt.-%.

Additives can be present up to an amount of about 50 wt.-% or up to about 40 wt.-% or up to about 35 wt.-%.

Typical ranges include from about 0 wt.-% to about 50 wt.-% or from about 0.005 wt.-% to about 40 wt.-% from about 0.01 wt.-% to about 35 wt.-%.

If additive(s) are present they are typically present in an amount sufficient and not detrimental to the desired effect or effects to be achieved.

It was found that a particular useful combination of the inventive composition comprise the cationically hardenable compound, the radiation sensitive starter, optionally an electron donor comprising an anthracene moiety and a component comprising a bi- or polycyclic aromatic amine structure, especially a bi- or polycyclic aromatic tert. amine or a bi- or polycyclic aromatic N,N-dialkyl (e.g. C1 to C12 or C1 to C6) amine. Typical examples include components comprising a naphthaline moiety like 1,8-bis(N,N-dimethylamino)-naphthaline and N,N-dimethyl-1-naphthylamine.

Such a combination can be useful if an improved Shore hardness is desired.

The cationically hardenable composition can comprise the individual components in the following amounts:
- (A) cationically hardenable compound comprising at least one aziridine moiety: from about 5 to about 90 wt.-% or from about 10 to about 80 wt.-% or from about 20 to about 70 wt.-%,
- (B) radiation sensitive starter: from about 0.25 to about 50 wt.-% or from about 0.5 to about 40 wt.-% or from about 1 to about 25 wt.-%,
- (C) sensitizer: from about 0.025 to about 50 wt.-% or from about 0.05 to about 40 wt.-% or from about 0.1 to about 25 wt.-%,
- (D) electron donor compound: from about 0 to about 50 wt.-% or from about 0.025 to about 40 wt.-% or from about 0.05 to about 25 wt.-%,
- (E) filler: from about 0 to about 80 wt.-% or from about 10 to about 75 wt.-% or from about 20 to about 70 wt.-%,
- (F) additive(s) or adjuvant(s): from about 0 to about 50 wt.-% or from about 0.005 to about 40 wt.-% or from about 0.01 to about 35 wt.-%, wt.-% with respect to the whole composition.

If the composition is to be used in the medical or dental field, the composition does typically not contain components which are not desirable form a toxicological standpoint of view and may easily leak from or migrate out of the mixed composition, especially when the composition is placed into a patients' mouth.

The invention is also directed to a process of production or manufacturing the composition. Such a process typically comprises at least one mixing or compounding step of the individual component of the composition. Mixing or compounding can be accomplished by using a kneader, speed-mixer or a dissolver. Typically, the filler(s) is/are added to the other components. This may facilitate the mixing procedure.

The curable composition of the invention can be obtained by combining (including mixing and kneading) the individual components of the composition, preferably under "safe light" conditions.

Suitable inert solvents may be employed if desired when formulating this mixture. Any solvent may be used which does not react appreciably with the components of the inventive compositions. Examples of suitable solvents include acetone, dichloromethane, acetonitrile, propylene carbonate, poly-THF and lactones (e.g. gamma-butyrolactone). A liquid material to be polymerized may be used as a solvent for another liquid or solid material to be polymerized. Solventless compositions can be prepared by simply dissolving the iodonium complex salt, sensitizer, and electron donor in the cationically polymerizable resin, with or without the use of mild heating to facilitate dissolution.

The individual components of the ternary photoinitiator system are provided in photopolymerizingly effective amounts (i.e., amounts effective to yield a photoinitiator system that can initiate photopolymerization of the cationically polymerizable resin or, more preferably, that can accelerate the rate of polymerization).

The composition according to the invention may be provided in separate parts and comprises at least a curable base paste and a catalyst or initiator paste comprising a catalyst, initiator or radiation sensitive starter suitable for curing at least part of the material of the base paste. This can be beneficial for improving the storage stability and/or shelf life.

Accordingly, the components of the composition can be included in a kit, where the contents of the composition are packaged to allow for storage of the components until they are needed.

When used, the components of the compositions can be mixed in the suitable amounts and applied using conventional techniques.

Thus, the invention also relates to a kit of parts, comprising a base paste and a catalyst paste separated from each other before use, wherein the base paste comprises the hardenable compound and the catalyst paste comprises the radiation sensitive starter and wherein the other optional components is/are present either in the base paste or the catalyst paste or in the base paste and the catalyst paste.

If a filler is present, it can be preferred, if the filler is present in the base paste only. This may be desirable from a chemical stability point of view. If the filler is present in the base paste only, the shelf life might be improved.

If the filler is present in the base paste, it is typically present in an amount of at least about 1 or at least about 5 or at least about 10 wt.-%, wt.-% with respect to the weight of the base paste. Typical ranges include from about 5 to about 70 or from about 10 to about 50 or from about 15 to about 45, with respect to the weight of the base paste.

The more equal the viscosity of the base paste compared to the catalyst paste is, and the lower the overall viscosity is, the easier the mixing can typically be achieved, especially if the mixing is done using a static mixing tip.

The volume ratios of catalyst paste and base paste can range from about 10:1 to about 1:10. Particularly preferred volume ratios of base paste to catalyst paste are from about 1:1 to about 10:1 or from about 2:1 to about 5:1 (e.g. 5 parts of base paste to 1 part of catalyst paste) or from about 2:1 to about 4:1.

The composition is typically stored in a container until use. Depending on the initiator system chosen, various containers can be suitable.

If the composition is provided as a one-component system, it can be stored in a container having only one chamber such as a capsule. The capsule has typically a cylindrical housing with a front and a rear end and a nozzle. The rear end of the housing is usually sealed with a movable piston. Typically, the dental composition is dispensed out of the capsule or container using an applier having a movable plunger (e.g. an application device having the shape of a caulk gun). Examples of suitable capsules or containers are described in U.S. Pat. No. 5,624,260, EP 1 340 472 A1, US 2007/0172789 A1, U.S. Pat. Nos. 5,893,714 and 5,865,803, the content of which with regard to the description of capsules or containers is herewith incorporated by reference.

If the composition should be applied into the sulcus of a teeth (i.e. the region between gum and hard dental tissue), using a container as described in WO 2009/151983 A2 can be beneficial due to its specific geometry. Such a device can be particularly useful in a dental retraction process.

Alternatively, if the composition is provided as a two-component system, it can be stored in a dual-chamber container or cartridge and is mixed before use.

Cartridges which can be used are described e.g. in US 2007/0090079 or U.S. Pat. No. 5,918,772, the disclosure of which is incorporated by reference. Cartridges which can be used are commercially available from SulzerMixpac AG (Switzerland).

Other suitable devices can be found in WO 2005/016783 A1, WO 2007/047381, WO 2007/104037, WO 2009/061884 and GB application no: 0906925.3.

If desired, the composition can also be stored in foil bags.

The disclosure of the above mentioned patents is herewith explicitly mentioned and regarded as part of the text of this invention and herewith incorporated by reference.

Generally, mixing and dosing of the components can be performed manually, e.g., by spatula (strand-length comparison) or a manually operated pre-filled dual cartridge dispenser with static mixing tips, or automated, using one of the various available devices available for such an automated task, preferably one of the devices mentioned in EP 0 232 733 A1, U.S. Pat. No. 6,135,631 or EP 0 863 088 A1 together with a dynamic mixing tip as mentioned in US 2004/0085854 or U.S. Pat. No. 6,244,740.

A further improvement of the handling properties of the composition can be seen in using an automatic mixing and metering systems for two-component compositions which have automatic conveying and mixing units, such as are described e.g. in U.S. Pat. Nos. 5,249,862, 5,286,105 and 5,419,460. The need for manual mixing of base pastes and catalyst pastes, above all when mixing larger quantities of material, can be eliminated, since this can take place automatically and within a short period of time. The result is usually a homogeneous product which is essentially free of air bubbles. Commercially available devices are distributed by 3M ESPE under the brand Pentamix™ or Pentamix™ 2 or Pentamix™ 3.

In practice, the composition (if provided as a two-component system) can be syringed through a static or dynamic mixing device onto a surface or into an impression tray or onto the patients' teeth or tissue and placed in the patients' mouth. The mixed pastes may also be applied using an applicator like an elastomer syringe.

The radiation which can be used for starting the hardening reaction of the radiation curable inventive composition is not particularly limited. All kind of radiation can be used, which is sufficient in energy. The more energetic the radiation is, the less time is typically required to start the hardening reaction.

Radiation having a wavelength in the range from about 250 to about 1000 nm or from about 350 to about 700 nm or from about 400 to about 500 nm was found to be useful.

In the dental and orthodontic area commercially polymerization lamps are sold under the trade name Elipar™ Freelight (3M ESPE).

If desired the composition can be cured at ambient temperature or a temperature which is typically present in the mouth of a patient (e.g. within a range from about 15 to 40° C.) at ambient pressure (e.g. within a range from about 850 to 1100 hPas).

Depending on the thickness and transparency of the composition to be cured, radiation is typically applied for a time period ranging from a few seconds to a few minutes, e.g. from about 1 s to about 120 s or from about 5 s to about 60 s from about 10 s to about 40 s.

The following combination of parameters was found to be particularly effective:

Wavelength: from about 400 to about 500 nm.
Duration: from about 2 s to about 2 min or from about 10 s to about 1 min or from about 20 s to about 40 s.
Power: from about 300 mW/cm$^2$ to about 2500 mW/cm$^2$ The exposure of the composition to radiation can be repeated, if desired.

The inventive composition can be used in various fields and areas.

These areas include hardcoats for a variety of substrates including various metals, glasses, plastics, papers, wood and the like. Other potential applications include graphic arts imaging (including curable inks, silverless imaging layers, an imaging layer on a projection plate, an imaging layer on a laser plate), photoresists, solder masks, electronic coatings, photocurable adhesives (including orthodontics), non-dental photocurable composites (including automotive parts or repair), a hard coat layer on an optical lens, or a coating on an optical fibre.

According to a particular embodiment, the inventive composition can be used in the dental field or as dental material.

In particular, the composition and the kit of parts are useful for taking a dental impression or as dental impression material or for use in a dental impression taking process or of preparing a dental impression material.

A composition or mixture comprising a iodonium salt, a sensitizer and cationically hardenable compound comprising at least two aziridine groups and having a molecular weight (Mn) in the range of about 200 to about 10,000 was found to be particularly useful, especially if used as a dental impression material or for making dental impressions.

The invention is also directed to the use of the inventive photoinitiator system for the production of a dental composition or material, the process of using comprising the steps of:
a) placing the composition comprising the photoinitiator system in contact with hard or soft dental tissue, and
b) applying radiation to harden the composition.

The composition can be used as dental impression material or for the production of crowns and/or bridges, including temporary or long term crowns and bridges. In the latter case, the composition is used as a mould to be filled with the (temporary or long term) crown and/or bridge material, which is typically based on polymerizable (meth)acrylates or similar chemical reactants.

The curable composition is especially useful for producing dental materials like precision impression materials, bite registration materials, duplicating materials, modelling materials, situation impression materials.

The composition can be used e.g. for making impressions of soft and hard dental tissue. This can be achieved simply, e.g. filling the material into a dental tray and putting the tray into the mouth of a patient.

If used in the dental field, curing is preferably carried out at a temperature below about 50° C. and preferably below about 40° C. A typical time for cure of curable compositions of the invention used for dental impressioning is within about 20 min, or preferably within about 10 min, after mixing the components of the composition. For dental duplicating applications or dental modelling applications that take place in the professional dental laboratory, cure times of up to 45 min is generally acceptable. In other applications (e.g., sealing, moulding, coating, adhesively fixing), other cure times may be typical and higher cure temperatures may be acceptable. Nevertheless, setting times in the range of about 30 min or about 1 hour can still be useful.

The material is generally regarded as cured, if the cured material fulfils the requirements for its use. For example, a dental precision impression material typically fulfils the requirements for its use when it fulfils the requirements of ISO 4823:2000 (such as compatibility with gypsum, strain in compression, recovery from deformation, detail reproduction, linear dimensional change).

According to another aspect, the invention is directed to kit of parts comprising a composition A and a composition B. Composition A and composition B differ from each other at least with respect to one property. Differentiating properties include consistency (e.g. determined according to ISO 4823), transparency and/or curing mechanism.

A difference in consistency or transparency might e.g. be caused by a different filler content or a different content of hardenable components present in the composition. Composition A is typically also a hardenable composition and can contain essentially the same components as composition B. Composition B is the composition as it is described in the text of the invention.

A difference in the curing mechanism can be achieved, e.g. if composition B contains a radiation sensitive starter and composition A contains a tri alkyl sulfonium initiator.

Such a kit might be useful in a process comprising the steps of
a) providing a composition A having the property A and a composition B having the property B, property A and property B being different from each other,
b) bringing composition B into contact with a surface,
c) applying radiation to composition B,
d) bringing composition A into contact with composition B,
e) removing the composition A and composition B from the surface.

Such a process can be beneficial if applied in the dental field.

Composition B can be applied e.g. to the surface of an individual tooth or several teeth. The hardening of composition B can be initiated by applying radiation. If desired, thereafter composition A can be applied and brought in contact with at least the surface of composition B.

Composition B is typically also a curable composition, but the curing reaction might be initiated by a different mechanism, i.e. not initiated by radiation. Such curing mechanisms include addition, condensation (e.g. of VPS materials) and ring-opening curing mechanisms (e.g. ring-opening of aziridines).

According to one embodiment composition A may comprise a cationically hardenable compound comprising at least one aziridine moiety and a sulfonium initiator being different from the radiation sensitive starter. Suitable sulfonium initiators for this embodiment include those described in formula I of US 2008/200585 and formula I of U.S. Pat. No. 4,167,618.

As composition A and composition B are in close contact, they typically adhere to each other during the hardening reaction. This may facilitate the removal of both, the hardened composition A and the hardened composition B in one step and may also help saving time and reducing stress for the practitioner e.g. when taking an impression of the dental hard and soft tissue of a patient.

Previously, the practitioner had to adjust the individual steps and often had not enough time for applying the impression material precisely to the tooth. The hardening reaction typically started immediately upon mixing the catalyst and base paste needed for producing the curable composition.

The inventive composition and the method of its application facilitate this former process, which is sometimes referred to as putty/wash or one-step technique in the dental field.

Thus, composition B—as described above—is typically used for making impressions of individual tooth, teeth or of the sulcus of the tooth or teeth, whereas composition A is used for recording the geometric relationship of the individual impressions achieved by curing composition B.

Typically, composition B is transparent, e.g. to the human eye. "Transparent" means that the translucency is in a range from about 20 to about 99% or from about 30 to about 95% (e.g. measured on a hardened sample being 1 mm thick against e.g. a $BaSO_4$ white background with an US/VIS spectrometer.

This may facilitate the inspection of the accuracy and/or quality of the application of the curable composition to the surface of the dental tissue and further adjustment of the impressioning composition or procedure, if desired. E.g. air inclusions, if present, can easily be detected.

In contrast to previous attempts where light curable impression materials were cured while being located in a dental impression tray, the present invention provides a composition and method where only a small amount of composition needs to be cured by radiation while being located on the surface of dental tissue. There is typically no need for using a either a transparent dental impression tray or a dental impression tray comprising a radiation source for the application and hardening of composition B. The impressioning procedure can be accomplished using the equipment which is already available to the dental practitioner.

Features and advantages of this invention are further illustrated by the following examples, which are in no way intended to be limiting thereof. The particular materials and amounts thereof recited in these examples, as well as other conditions and details, should not be construed to unduly limit this invention.

EXAMPLES

Unless otherwise indicated, all parts and percentages are on a weight basis, all water is deionized water and all molecular weights are weight average molecular weight. Moreover, unless otherwise indicated all experiments were conducted at ambient conditions (23° C.; 1013 mbar).

General Procedures:

Mixing was typically done using a speedmixer (Speed-Mixer DAC 150 FVZ, Hauschild Engeneering) with a speed of about 2400 rounds per minute until a homogeneous paste was obtained (typically within about 2 to about 4 min).

Photopolymerization was initiated using an Elipar™ S10 dental photocuring source (3M ESPE). The source emitted radiation predominantly in the range of about 430-480 nm and had a light intensity of about 1200 $mW/cm^2$.

Description of Measurements

Depth of Cure Test Method A

Depth of cure (i.e., cure depth) was analyzed similar to ISO 4049 by packing a paste sample into a cylindrical metal curing mould (15 mm deep, 4 mm diameter) and curing the sample for 40 s with an ELIPAR™ S10 Standard (1200 $mW/cm^2$) (3M ESPE Company). The cured sample was removed from the mould and uncured paste was scraped off of the sample with a plastic applicator after less than about one minute of curing. Results were reported as the average of two replicates.

Shore Hardness A

Shore Hardness A is a very convenient method to obtain data about the degree of vulcanization. The value of Shore Hardness is a common number in dentistry to characterize a cured impression material.

Measurements were done according to DIN 53505. For determination of the values three independent measurements were performed. A "Härteprüfgerät Zwick 3100/Prüfeinrichtung 7206" (Zwick GmbH &Co. Ulm) was used as the measuring device.

Abbreviations

TABLE 1

| | Name | Function |
| --- | --- | --- |
| EDMO | 3-Ethyl-1,6-dimethoxy-anthracen | Electron donor |
| Ant | Anthracene | Electron donor |
| DMAEB | Dimethylaminoethylbenzoat | Electron donor |
| IPB | Tolyl-cumyl-Iodonium (pentafluorophenyl) borat | Radiation sensitive starter |
| IPP | Diphenyl-Iodonium hexafluorophosphate | Radiation sensitive starter |
| IPA | Octylphenyl-phenyl-Iodonium hexafluoroantimonate | Radation sensitive starter |
| FeP | (η5-2,4-cyclopentadien-1-yl) [1,2,3,4,5,6-η)-(1-methylethyl)benzene]-iron(II)-hexafluorophosphate | Radiation sensitive starter |
| SA | Triarylsulfonium hexafluoroantimonate, 50-% solution in propylene carbonate | Radiation sensitive starter |
| Rhodorsil 2074 | 4-Methyl-[4-(1-methylethyl)phenyl]iodonium-tetrakis(pentafluorphenyl)borat | Radiation sensitive starter |
| FS1 | Aerosil 200 | Filler |
| FS2 | Celatom MW25 | Filler |
| DBT | Dibenyltoluol | Diluent |
| gBL | gamma-Butyrolacton | Diluent |

TABLE 1-continued

| Name | | Function |
|---|---|---|
| PT650 | Linear Polytetrahydrofurane (Mn = 650) | Diluent |
| DD-PE | Copolymer of THF and ethylene oxide (ration 2:1; molecular weight: 6,000; esterified with acetic anhydride as described in U.S. Pat. No. 6,677,393 (preparation example). | Diluent |
| CQ | Camphercinon (Sigma Aldrich) | Sensitizer |
| AZ-PE | Aziridino-functionalized polyether (EO (ethylene oxide)/THF (tetrahydrofuran) polyether back bone; $M_n$ 6000) with a low content of cyclic polyether compounds as described in U.S. Pat. No. 6,383,279 | Hardenable compound, |
| Epox | mixture of the following two components: silane, methylbis[2-(7-oxabicyclo-[4.1.0]hept-3-yl)ethyl]phenyl and 1,3,5,7-tetrakis(1,2-ethanediyl-3,4-epoxycyclohexyl)-1,3,5,7-tetramethylcyclotetrasiloxane; as described for "Monomer Composition 2" in U.S. patent application Ser. No. 2003/0035899 (Klettke et al.) | Hardenable compound |
| TINUVIN 328 | 2-(2-Hydroxy-3,5-di-tert-amylphenyl)benzotriazole | Stabilizer |
| TINUVIN 292 | Bis(1,2,2,6,6-pentamethyl-4-piperidinyl) sebacate | Stabilizer |
| 2-Prop | 2-Propanol | Chain transfer agent |
| TERATHANE 650 | Poly THF | |

The following compositions were prepared and tested (Table 2):

TABLE 2

| | Ex. 1 | Ex. 2 | Ex. 3 | Ex. 4 | Ex. 5 | Ex. 6 | Ex. 7 | Ex. 8 | C. Ex. 1 | C. Ex. 2 |
|---|---|---|---|---|---|---|---|---|---|---|
| AzPE | 79.30 | 76.10 | 64.70 | 77.20 | 64.90 | 69.10 | 60.80 | 71.70 | 84.40 | 84.40 |
| Epox | | | | | | | 21.3 | | | |
| IPP | 2.20 | | | | | | | | | |
| IPB | | | | 4.36 | 3.65 | 3.85 | 3.95 | 4.30 | | |
| IPA | | 5.30 | 4.51 | | | | | | | |
| SA | | | | | | | | | 7.00 | |
| FeP | | | | | | | | | | 3.60 |
| CC | 0.62 | 1.30 | 1.11 | 0.72 | 0.61 | 0.64 | 0.80 | 1.20 | | |
| EDMO | 0.18 | 0.20 | 0.17 | | | | 0.19 | 0.20 | | |
| Ant | | 0.10 | 0.09 | | | | | 0.10 | | |
| DMAEB | | | | 0.52 | 0.44 | 0.47 | | | | |
| FS1 | | 15 | | | 9.90 | 10.50 | | 12.50 | | |
| gBL | 17.70 | 17.00 | 14.50 | | | | | | | |
| PT650 | | | | 17.20 | 14.50 | 15.44 | | 10.00 | | |
| DBT | | | | | | | 13.00 | | 8.60 | 12.00 |
| 2-Prop | | | | | | 6.00 | | | | |

The pastes were prepared by mixing the components as given in Table 2 with a speedmixer (SpeedMixer DAC 150 FVZ, Hauschild Engineering) at a speed of about 2400 rounds/min until a homogenous paste was obtained. Some pastes were tested as described above with respect to curing depth. The results are given in Table 3.

TABLE 3

| Example | Curing depth after 40 s illumination [mm] | Curing depth after 20 s illumination [mm] |
|---|---|---|
| Ex. 1 | 7.5 | 5.9 |
| Ex. 2 | 7.2 | 3.7 |
| Ex. 4 | 7.5 | 7.3 |
| Ex. 5 | 7.5 | 6.7 |
| C. Ex. 1 | 0 | 0 |

Besides the above mentioned Examples the following Examples where prepared in addition and tested with respect to Shore Hardness A.

Example 9

No Filler

The composition was prepared by mixing AZ-PE (13.07 g), CQ (0.028 g), RHODORSIL 2074 (0.48 g) and γ-Butyrolacton (2.08 g; Sigma Aldrich).

The Shore hardness A of a test specimen after 40 s illumination per each side (front and back side of the test specimen) was 48.

Example 10

With Filler

The composition was prepared by mixing AZ-PE (13.08 g), CQ (0.028 g), RHODORSIL 2074 (0.43 g), Celatom MW25 and γ-Butyrolacton (2.07 g).

The Shore hardness A of a test specimen after 40 s illumination per each side (front and back side of the test specimen) was 49.

Example 11

With Stabilizer

The composition with stabilizing agent (N,N-Dimethyl-1-naphthylamin) was prepared by mixing AZ-PE (13.05 g), CQ (0.029 g), RHODORSIL 2074 (0.41 g), γ-Butyrolacton (2.02 g) and N,N-Dimethyl-1-naphthylamin (0.24 g).

The Shore hardness A of a test specimen after 40 s illumination per each side (front and back side of the test specimen) was 54.

Example 12

With Stabilizer

The composition was prepared by mixing AZ-PE (13.14 g), CQ (0.029 g), RHODORSIL 2074 (0.42 g), γ-Butyrolacton (2.00 g), TINUVIN 292 (0.029 g), TINUVIN 328 (0.051 g) and 1,8-Bis(N,N-dimethylamino)-naphthalin (0.10 g).

The Shore hardness A of a test specimen after 40 s illumination per each side (front and back side of the test specimen) was 38.

Example 13

With Stabilizer

The composition was prepared by mixing AZ-PE (13.06 g), CQ (0.028 g), RHODORSIL 2074 (0.41 g), γ-Butyrolacton (2.01 g) and 1,8-Bis(N,N-dimethylamino)-naphthalin (0.028 g).

The Shore hardness A of a test specimen after 40 s illumination per each side (front and back side of the test specimen) was 38.

Example 14

With Electron Donor

The composition with electron donor compounds (Anthracen and EDMO) was prepared by mixing AZ-PE (16.54 g), CQ (0.027 g), RHODORSIL 2074 (0.79 g), TERATHANE 650 (3.50 g), Anthracene (0.011 g) and EDMO (0.003 g).

The Shore hardness A of a test specimen after 40 s illumination per each side (front and back side of the test specimen) was 50.

Example 15

Without Filler

The composition was prepared by mixing AZ-PE (13.28 g), CQ (0.024 g), IPA (0.31 g; Hampford Research INC) and γ-Butyrolacton (2.02 g; Sigma Aldrich) with a speedmixer (SpeedMixer DAC 150 FVZ, Hauschild Engeneering).

The Shore hardness A of a test specimen after 40 s illumination per each side (front and back side of the test specimen) was 45.

Example 16

Without Filler

The original composition was prepared by mixing AZ-PE (14.21 g), CQ (0.029 g), RHODORSIL 2074 (0.40 g) and propylene carbonate (2.10 g; Sigma Aldrich).

The Shore hardness A of a test specimen after 40 s illumination per each side (front and back side of the test specimen) was 36.

Example 17

Without CQ

The original composition was prepared by mixing AZ-PE (12.20 g), 2-Aminoanthracen (0.023 g), RHODORSIL 2074 (0.43 g), N,N-Dimethyl-1-naphthylamin (0.256 g) and γ-Butyrolacton (2.00 g)

The Shore hardness A of a test specimen after 60 s illumination per each side (front and back side of the test specimen) was approximately 25.

Example 18

Without Lewis Acid

The composition was prepared by mixing component 1 (100% AZ-PE) with component 2 (1.17% CQ, 17.12% RHODORSIL 2074 and 81.71% DD-PE in a dispensing cartridge (Garant cartridge with mixing tip) with the ratio 4:1.

The Shore hardness A of a test specimen after 40 s illumination per each side (front and back side of the test specimen) was 41.

Example 19

With Lewis Acid

The composition was prepared by mixing component 1 (100% AZ-PE) with component 2 (0.95% CQ, 13.65% RHODORSIL 2074, 64.88% DD-PE, 19.44% γ-Butyrolacton and 0.96% Aluminiumchlorid Hexahydrate in a dispensing cartridge (Garant cartridge with mixing tip) with the ratio 4:1.

The Shore hardness A of a test specimen after 40 s illumination per each side (front and back side of the test specimen) was 32.

Comparative Example 3

Without Iodonium Salt

The iodonium salt free composition with electron donor compounds (Anthracen and EDMO) was prepared by mixing AZ-PE (13.16 g), CQ (0.027 g), TERATHANE 650 (3.57 g), Anthracene (0.012 g) and EDMO (0.0028 g).

No curing was observed after 40 s illumination per each side (front and back side of the test specimen) using an Elipar™ S10 dental photocuring source (3M ESPE).

Comparative Example 4

Without Iodonium Salt

The iodonium salt-free composition without CQ and iodonium salt was prepared by mixing AZ-PE (13.06 g), 2-Aminoanthracen (0.022 g), N,N-Dimethyl-1-naphthylamin (0.263 g) and γ-Butyrolacton (2.04 g).

No curing was observed after 40 s illumination per each side (front and back side of the test specimen) using an Elipar™ S10 dental photocuring source (3M ESPE).

The invention claimed is:

1. A radiation curable composition comprising
   (A) a cationically hardenable compound comprising at least one or two aziridine moieties having an aziridine equivalent weight in the range of about 250 to about 25,000 g/equivalent, and
   (B) a radiation sensitive starter, the radiation sensitive starter comprising an iodonium salt.

2. The composition according to claim 1, the cationically hardenable compound comprising a backbone containing moieties selected from polyether, polyesters, polyamides, polyurethanes, silicones and combinations thereof.

3. The composition according to claim 1, the aziridine moiety being characterized by the following formula

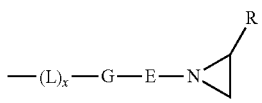

wherein
   R represents H, C1-C12 alkyl, C2-C12 alkenyl, C2-C12 alkinyl, C7-C15 alkylaryl, C7-C15 arylalkyl or C3-C12 cycloalkyl, and wherein hydrogen atoms can be replaced by Cl or F and/or wherein up to about 5 carbon atoms may be replaced by atoms or group of atoms selected from O, CO, N or S,
   E represents a C1-C18 branched or unbranched hydrocarbon chain wherein up to about 5 carbon atoms can be replaced by atoms or group of atoms selected from O, CO, N or S,
   G represents a group selected from C(O)O, C(O)NR, C(O), C(O)C(O), C(O)(CH$_2$)$_m$C(O) with m=1 to 10, C(S)NR or CH$_2$,
   L represents O, S or NR, with x=0 or 1.

4. The composition according to claim 1 comprising a sensitizer, the sensitizer being able to absorb radiation in the region of about 250 to about 1000 nm.

5. The composition according to claim 4, the sensitizer being selected from components comprising alpha di-ketones, coumarin dyes, xanthene dyes, fluorine dyes, fluorescein dyes, aminoketone dyes, p-substituted aminostyryl ketone compounds, mixtures and combinations thereof.

6. The composition according to claim 1 comprising an electron donor compound.

7. The composition according to claim 6, the electron donor compound being selected from components comprising an anthracene, biphenylene, aromatic tertiary amine or aromatic ether moiety, mixtures and combinations thereof.

8. The composition according to claim 1 comprising one or more additive(s) selected from retarders, rheology modifier(s), thixotropic agent(s), diluting agent(s), inhibitor(s), pigment(s), dye(s), plasticizer(s), odorous substance(s), flavouring(s), stabilizer(s), mixtures and combinations thereof.

9. The composition according to of claim 1 comprising the individual components in the following amounts:
   (A) cationically hardenable compound comprising at least one aziridine moiety: from about 5 to about 90 wt.-%,
   (B) radiation sensitive starter: from about 0.25 to about 50 wt.-%,
   (C) sensitizer: from about 0 to about 50 wt.-%,
   (D) electron donor compound: from about 0 to about 50 wt.-%,
   (E) filler: from about 0 to about 80 wt.-%,
   (F) additives: from about 0 to about 50 wt.-%, wt.-% with respect to the weight of the whole composition.

10. The composition according to claim 1, being characterized by at least one of the following parameters after hardening:
    Tensile strength (according to DIN 53504): at least about 0.2 MPa,
    Elongation at break (according to DIN 53504): at least about 30%,
    Recovery from deformation (according to ISO 4823): at least about 90%,
    Shore A hardness (according to DIN 53505; 24 h): equal to or above about 10.
    Elastic deformation (according to ISO 4823): from about 0.2 to about 20%.

11. A kit of parts for preparing an elastomeric composition comprising part I and part II,
    part I comprising a cationically hardenable compound comprising at least one or two aziridine moieties having an aziridine equivalent weight in the range of about 250 to about 25,000 g/equivalent,
    part II comprising a radiation sensitive starter comprising an iodonium salt,
    wherein the optional compound(s) selected from sensitizer(s), electron donor(s) or additive(s) are either present in part I or part II or part I and part II, wherein the compounds are as described in claim 1.

12. A kit of parts for preparing an elastomeric composition comprising a composition A having the consistency A and a composition B having the consistency B, consistency A and consistency B being different from each other and composition B corresponding to the composition as described in claim 1.

13. A method comprising the steps of a) providing a composition as described in claim 1, b) curing the composition by radiation.

14. The method of claim 13 comprising the steps of
    a. providing a composition A having the consistency A and a composition B having the consistency B, consistency A and consistency B being different from each other and composition B being as described in claim 1,
    b. bringing composition B into contact with a surface,
    c. applying radiation to composition B,
    d. bringing composition A into contact with composition B,
    e. removing the composition A and composition B from the surface.

15. The method of claim 13, wherein composition A comprises a cationically hardenable compound comprising on average at least two aziridine moieties.

* * * * *

UNITED STATES PATENT AND TRADEMARK OFFICE
CERTIFICATE OF CORRECTION

| | |
|---|---|
| PATENT NO. | : 8,921,440 B2 |
| APPLICATION NO. | : 13/640342 |
| DATED | : December 30, 2014 |
| INVENTOR(S) | : Wolfgang Weinmann |

It is certified that error appears in the above-identified patent and that said Letters Patent is hereby corrected as shown below:

Title Page

Column 1

First page, (Inventors), Line 1, delete "Wilheim" and insert -- Wilhelm --, therefor.

Specification

Column 1

Line 66, delete "i.a." and insert -- i.e. --, therefor.

Column 3

Line 22, delete "time" and insert -- time. --, therefor.

Column 6

Line 33, delete "wettabilty" and insert -- wettability --, therefor.

Column 7

Lines 64-65, delete "10 l/s to 100 l/s in 10 l/s and/or 5 l/s steps." and insert -- 10 l/s to 100 l/s in 10 l/s and/or 5 l/s steps). --, therefor.

Column 8

Line 41, delete "tetrahydrofurane" and insert -- tetrahydrofuran --, therefor.

Signed and Sealed this
Twenty-seventh Day of October, 2015

Michelle K. Lee
*Director of the United States Patent and Trademark Office*

Specification

Column 8

Line 42, delete "epichlorohydrine" and insert -- epichlorohydrin --, therefor.

Column 8

Line 56, delete "tetrahydrofurane." and insert -- tetrahydrofuran. --, therefor.

Column 9

Line 14, delete "azirdine" and insert -- aziridine --, therefor.

Column 10

Line 38, delete "C(O)(CH2)mC(O)" and insert -- $C(O)(CH_2)_mC(O)$ --, therefor.

Column 11

Line 34 (approx.), delete "hexacrylate," and insert -- hexaacrylate, --, therefor.

Column 11

Lines 35-36 (approx.), delete "bis[1-(3-acryloxy-2-hydroxy)]p-propoxyphenyldimethylmethane," and insert -- bis[1-(3-acryloxy-2-hydroxy)]-p-propoxyphenyldimethylmethane, --, therefor.

Column 12

Line 27, delete "$B(C_6(CF_3)_5)_{4,}^-,$" and insert -- $B(C_6(CF_3)_5)_4^-$, --, therefor.

Column 14

Lines 29-30, delete "iron-hexafluoroantimonat," and insert -- iron-hexafluoroantimonate, --, therefor.

Column 14

Line 31, delete "iron-tetrafluorborat." and insert -- iron-tetrafluoroborate. --, therefor.

Column 15

Line 9, delete "sensitzer" and insert -- sensitizer --, therefor.

Specification

Column 16

Line 5, delete "acenaphthaquinone," and insert -- acenaphthoquinone, --, therefor.

Column 16

Line 12, delete "hydroxybenzil;" and insert -- hydroxybenzyl; --, therefor.

Column 17

Line 46, delete "iso-propy," and insert -- iso-propyl, --, therefor.

Column 18

Line 8, delete "anthacenes" and insert -- anthracenes --, therefor.

Column 18

Line 46, delete "relaced" and insert -- replaced --, therefor.

Column 18

Line 63, (approx.), delete "alkylhio," and insert -- alkythio, --, therefor.

Column 20

Line 1, delete "nephelinsyenite," and insert -- nephelinesyenite, --, therefor.

Column 21

Line 17, delete "nephelinsyenit," and insert -- Nephelinesyenite, --, therefor.

Column 22

Line 21, delete "naphthaline" and insert -- naphthalene --, therefor.

Column 23

Line 2, delete "solfonic" and insert -- sulfonic --, therefor.

Column 23

Line 19, delete "solfonic" and insert -- sulfonic --, therefor.

Specification

Column 24

Line 61, delete "I. 46 to col. 6. I. 52" and insert -- l. 46 to col. 6. l. 52 --, therefor.

Column 24

Line 63, delete "I. 1 to p. 5, I. 16" and insert -- l. 1 to p. 5, l. 16 --, therefor.

Column 26

Lines 37, delete "naphthaline" and insert -- naphthalene --, therefor.

Column 26

Lines 37-38, delete "naphthaline" and insert -- naphthalene --, therefor.

Column 32

Line 18, delete "Engeneering)" and insert -- Engineering) --, therefor.

Columns 31-32

Line 7, Table 1, delete "Radation" and insert -- Radiation --, therefor.

Columns 31-32

Line 13, Table 1, delete "pentafluorphenyl" and insert -- pentafluorophenyl --, therefor.

Columns 31-32

Line 16, Table 1, delete "Dibenyltoluol" and insert -- Dibenzyltoluene --, therefor.

Columns 33-34

Line 2, Table 1-continued, delete "Polytetrahydrofurane" and insert -- Polytetrahydrofuran --, therefor.

Columns 33-34

Line 9, Table 2, delete "CC" and insert -- CQ --, therefor.

Specification

Column 35

Line 56, delete "Engeneering)." and insert -- Engineering). --, therefor.

Column 36

Line 12, delete "(2.00 g)" and insert -- (2.00 g). --, therefor.

Claims

Column 37

Line 26, in Claim 3, delete "C1 or F" and insert -- Cl or F --, therefor.

Column 37

Line 42, in Claim 5, delete "fluorine" and insert -- fluorone --, therefor.

Column 37

Line 54, in Claim 8, delete "plastizer(s)," and insert -- plasticizer(s), --, therefor.

Column 37

Line 56, in Claim 9, delete "to of" and insert -- to --, therefor.

Column 38

Line 20, in Claim 10, delete "about 10." and insert -- about 10, --, therefor.